US009089478B2

(12) United States Patent
Whitcup et al.

(10) Patent No.: US 9,089,478 B2
(45) Date of Patent: Jul. 28, 2015

(54) PERIPHERALLY ADMINISTERED VISCOUS FORMULATIONS

(71) Applicant: Allergan, Inc., Irvine, CA (US)

(72) Inventors: Scott M. Whitcup, Laguna Hills, CA (US); Michael R. Robinson, Irvine, CA (US); Robert T. Lyons, Laguna Hills, CA (US); John T. Trogden, Villa Park, CA (US)

(73) Assignee: Allergen, Inc., Irvine, CA (US)

( * ) Notice: Subject to any disclaimer, the term of this patent is extended or adjusted under 35 U.S.C. 154(b) by 0 days.

(21) Appl. No.: 14/463,337

(22) Filed: Aug. 19, 2014

(65) Prior Publication Data

US 2014/0356438 A1 Dec. 4, 2014

Related U.S. Application Data

(60) Division of application No. 11/828,561, filed on Jul. 26, 2007, now Pat. No. 8,846,094, which is a continuation-in-part of application No. 11/741,366, filed on Apr. 27, 2007, now abandoned, which is a continuation-in-part of application No. 11/354,415, filed on Feb. 14, 2006, now abandoned, which is a continuation-in-part of application No. 10/966,764, filed on Oct. 14, 2004, now abandoned.

(60) Provisional application No. 60/519,237, filed on Nov. 12, 2003, provisional application No. 60/530,062, filed on Dec. 16, 2003.

(51) Int. Cl.

| | |
|---|---|
| ***A61K 9/14*** | (2006.01) |
| ***A61K 9/00*** | (2006.01) |
| ***A61K 31/56*** | (2006.01) |
| ***A61K 31/573*** | (2006.01) |
| ***A61K 31/715*** | (2006.01) |
| ***A61K 47/02*** | (2006.01) |
| ***A61K 47/34*** | (2006.01) |
| ***A61K 47/36*** | (2006.01) |
| ***A61K 47/40*** | (2006.01) |
| ***A61K 31/58*** | (2006.01) |

(52) U.S. Cl.

CPC ............. *A61K 9/0019* (2013.01); *A61K 9/0048* (2013.01); *A61K 31/56* (2013.01); *A61K 31/573* (2013.01); *A61K 31/58* (2013.01); *A61K 31/715* (2013.01); *A61K 47/02* (2013.01); *A61K 47/34* (2013.01); *A61K 47/36* (2013.01); *A61K 47/40* (2013.01)

(58) Field of Classification Search

CPC .................................................... A61K 9/0019
USPC .......................................................... 424/488
See application file for complete search history.

(56) References Cited

U.S. PATENT DOCUMENTS

| | | | | |
|---|---|---|---|---|
| 3,396,081 | A | 8/1968 | Billek | |
| 3,845,770 | A | 11/1974 | Theeuwes et al. | |
| 3,916,899 | A | 11/1975 | Theeuwes et al. | |
| 4,008,864 | A | 2/1977 | Torphammar et al. | |
| 4,014,335 | A | 3/1977 | Arnold | |
| 4,052,505 | A | 10/1977 | Higuchi et al. | |
| 4,057,619 | A | 11/1977 | Higuchi et al. | |
| 4,063,064 | A | 12/1977 | Saunders et al. | |
| 4,088,864 | A | 5/1978 | Theeuwes et al. | |
| 4,144,317 | A | 3/1979 | Higuchi et al. | |
| 4,158,005 | A | 6/1979 | Bodor et al. | |
| 4,186,184 | A | 1/1980 | Zaffaroni | |
| 4,190,642 | A | 2/1980 | Gale et al. | |
| 4,200,098 | A | 4/1980 | Ayer et al. | |
| 4,281,654 | A | 8/1981 | Shell et al. | |
| 4,285,987 | A | 8/1981 | Ayer et al. | |
| 4,303,637 | A | 12/1981 | Shell et al. | |
| 4,304,765 | A | 12/1981 | Shell et al. | |
| 4,327,725 | A | 5/1982 | Cortese et al. | |
| 4,383,992 | A | 5/1983 | Lipari | 424/438 |

(Continued)

FOREIGN PATENT DOCUMENTS

| | | |
|---|---|---|
| CA | 1333770 | 10/1988 |
| EP | 0 197 718 | 3/1986 |

(Continued)

OTHER PUBLICATIONS

Adams, Mark, An Analysis of Clinical Studies of the Use of Crosslinked Hyaluronan, Hylan, in the Treatment of Osteoarthritis, The Journal of Rheumatology, 1993, 16-18, 20 (39).

(Continued)

*Primary Examiner* — Jake Vu

(74) *Attorney, Agent, or Firm* — Brigitte C. Phan; Ted A. Chan; Debra D. Condino

(57) ABSTRACT

Viscous formulations and methods of using such compositions, useful for intramuscular and intra-articular injection are provided to treat peripheral conditions. Such compositions can include triamcinolone particles present in a therapeutically effective amount, a viscosity inducing component, and an aqueous carrier component. The compositions have viscosities of at least about 10 cps or about 100 cps at a shear rate of 0.1/second. In a preferred embodiment, the viscosity is in the range of from about 80,000 cps to about 300,000 cps. In a most preferred embodiment, the viscosity is in the range of from about 140,000 cps to about 280,000 cps at a shear rate of 0.1/second at 25° C. The compositions advantageously suspend the triamcinolone particles for prolonged periods of time.

8 Claims, 4 Drawing Sheets

(56) References Cited

Figure 1:
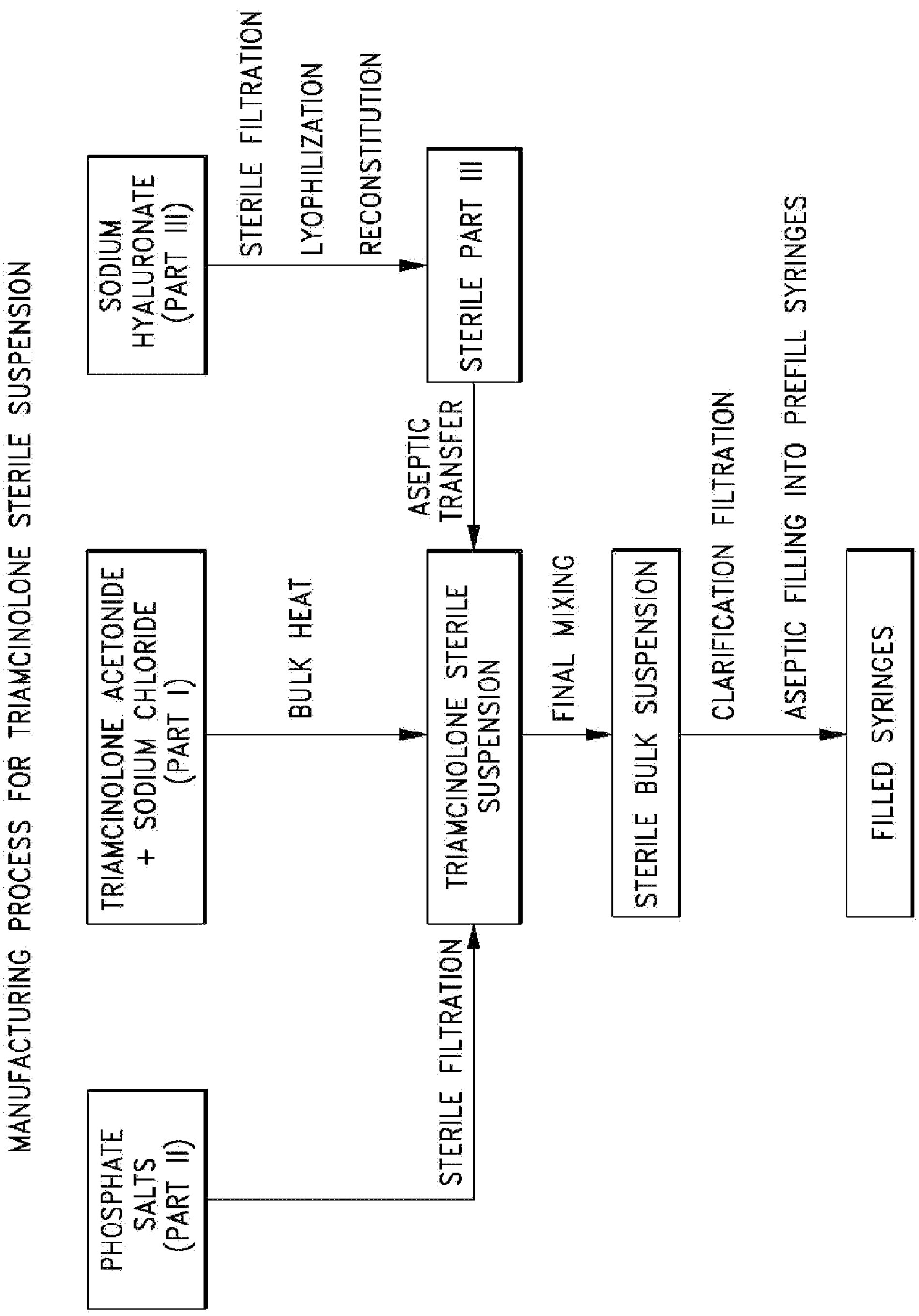

U.S. PATENT DOCUMENTS 4,396,625 A 8/1983 Yamamori et al.
4,425,346 A 1/1984 Horlington
4,474,451 A 10/1984 Mizokami
4,478,818 A 10/1984 Shell et al.
4,494,274 A 1/1985 Thurlow
4,521,210 A 6/1985 Wong
4,599,353 A 7/1986 Bito
4,636,524 A 1/1987 Balazs et al.
4,649,151 A 3/1987 Dougherty et al.
4,656,186 A 4/1987 Bommer et al.
4,668,506 A 5/1987 Bawa
4,675,338 A 6/1987 Bommer et al.
4,693,885 A 9/1987 Bommer et al.
4,712,500 A 12/1987 Montandon
4,713,448 A 12/1987 Balazs et al.
4,727,064 A 2/1988 Pitha
4,853,224 A 8/1989 Wong ............................ 424/427
4,863,457 A 9/1989 Lee
4,865,846 A 9/1989 Kaufman
4,866,168 A 9/1989 Dougherty et al.
4,920,104 A 4/1990 DeVore et al.
4,932,934 A 6/1990 Dougherty et al.
4,935,498 A 6/1990 Sessler et al.
4,941,874 A 7/1990 Sandow et al.
4,959,217 A 9/1990 Sanders et al.
4,968,715 A 11/1990 Dougherty et al.
4,981,871 A 1/1991 Abelson
4,997,652 A 3/1991 Wong ............................ 424/428
5,002,962 A 3/1991 Pandey et al.
5,017,579 A 5/1991 Gubin et al.
5,019,400 A 5/1991 Gombotz et al.
5,028,621 A 7/1991 Dougherty et al.
5,034,413 A 7/1991 Chan et al.
5,075,115 A 12/1991 Brine
5,077,049 A 12/1991 Dunn et al.
5,089,509 A 2/1992 Chandraratna
5,093,349 A 3/1992 Pandey et al.
5,098,443 A 3/1992 Parel et al.
5,099,013 A 3/1992 Balazs et al.
5,100,431 A 3/1992 Buster et al.
5,106,615 A 4/1992 Dikstein
5,143,724 A 9/1992 Leshchiner et al.
5,164,188 A 11/1992 Wong ............................ 424/428
5,166,331 A 11/1992 Della Valle et al.
5,169,638 A 12/1992 Dennis et al.
5,171,741 A 12/1992 Dougherty
5,173,504 A 12/1992 Dougherty
5,190,966 A 3/1993 Dougherty
5,198,460 A 3/1993 Pandey et al.
5,209,926 A 5/1993 Babcock .................... 424/78.04
5,256,408 A 10/1993 Babcock et al.
5,268,178 A 12/1993 Calhoun et al.
5,300,114 A 4/1994 Gwon et al.
5,314,905 A 5/1994 Pandey et al.
5,324,519 A 6/1994 Dunn et al.
5,324,718 A 6/1994 Loftsson ......................... 514/58
5,332,582 A 7/1994 Babcock et al.
5,356,629 A 10/1994 Sander et al.
5,378,475 A 1/1995 Smith et al. ................... 424/473
5,385,887 A 1/1995 Yim et al.
5,427,778 A 6/1995 Finkenaur et al. ......... 424/78.08
5,438,071 A 8/1995 Clauss et al.
5,443,505 A 8/1995 Wong et al. ....................... 623/4
5,459,159 A 10/1995 Pandey et al.
5,466,233 A 11/1995 Weiner et al.
5,487,897 A 1/1996 Polson et al.
5,494,901 A 2/1996 Javitt et al.
5,501,856 A 3/1996 Ohtori et al.
5,504,074 A 4/1996 D'Amato et al.
5,516,522 A 5/1996 Peyman et al.
5,552,160 A 9/1996 Liversidge et al.
5,565,188 A 10/1996 Wong et al.
5,576,311 A 11/1996 Guy .............................. 514/179
5,587,371 A 12/1996 Sessler et al.
5,587,479 A 12/1996 Makovec et al.
5,597,897 A 1/1997 Ron et al.
5,655,832 A 8/1997 Pelka et al.
5,656,297 A 8/1997 Bernstein et al.
5,688,819 A 11/1997 Woodward et al.
5,702,716 A 12/1997 Dunn et al.
5,707,643 A 1/1998 Ogura
5,717,030 A 2/1998 Dunn et al.
5,747,061 A 5/1998 Amselem et al.
5,766,242 A 6/1998 Wong et al.
5,770,589 A 6/1998 Billson ......................... 514/174
5,776,699 A 7/1998 Klein et al.
5,780,044 A 7/1998 Yewey et al.
5,798,349 A 8/1998 Levy et al.
5,824,072 A 10/1998 Wong
5,824,074 A 10/1998 Koch
5,869,079 A 2/1999 Wong et al.
5,877,207 A 3/1999 Klein et al.
5,882,682 A 3/1999 Rork et al.
5,906,920 A 5/1999 Evans et al.
5,913,884 A 6/1999 Trauner et al.
5,919,970 A 7/1999 Song et al.
5,922,773 A 7/1999 Lipton et al.
5,958,954 A 9/1999 Klein et al.
6,051,576 A 4/2000 Ashton et al.
6,066,675 A 5/2000 Wen et al.
6,074,661 A 6/2000 Olejnik et al.
6,107,347 A 8/2000 Francese et al.
6,143,314 A 11/2000 Chandrashekar et al.
6,217,869 B1 4/2001 Meyer et al.
6,217,895 B1 4/2001 Guo et al. ..................... 424/427
6,225,303 B1 5/2001 Miller et al.
6,251,876 B1 6/2001 Bellini et al. ................... 514/54
6,258,319 B1 7/2001 Hearst et al.
6,261,583 B1 7/2001 Dunn et al.
6,270,492 B1 8/2001 Sinofsky
6,270,749 B1 8/2001 Blumenkranz et al.
6,271,216 B1 8/2001 Mello et al.
6,271,220 B1 8/2001 Garst et al.
6,274,614 B1 8/2001 Richter et al.
6,290,713 B1 9/2001 Russell
6,294,361 B1 9/2001 Horowitz et al.
6,306,426 B1 10/2001 Olejnik et al.
6,317,616 B1 11/2001 Glossop
6,319,273 B1 11/2001 Chen et al.
6,331,313 B1 12/2001 Wong et al.
6,357,568 B1 3/2002 Chen
6,369,116 B1 4/2002 Wong et al.
6,387,409 B1 5/2002 Khan et al.
6,395,293 B2 5/2002 Polson et al.
6,395,294 B1 5/2002 Peyman ........................ 424/427
6,403,649 B1 6/2002 Woodward et al.
6,407,079 B1 6/2002 Müller et al.
6,455,062 B1 9/2002 Olejnik et al.
6,461,631 B1 10/2002 Dunn et al.
6,482,854 B1 11/2002 Lipton et al.
6,497,729 B1 12/2002 Moussy et al.
6,537,568 B2 3/2003 Olejnik et al.
6,548,078 B2 4/2003 Guo et al. ..................... 424/423
6,565,871 B2 5/2003 Roser et al.
6,565,874 B1 5/2003 Dunn et al.
6,573,280 B2 6/2003 Dreyer
6,595,945 B2 7/2003 Brown
6,645,945 B1 11/2003 Radomsky et al. ............. 514/54
6,699,493 B2 3/2004 Wong
6,713,081 B2 3/2004 Robinson et al.
6,713,268 B2 3/2004 Woodward et al.
6,723,353 B2 4/2004 Beck et al.
6,726,918 B1 4/2004 Wong et al.
6,765,012 B2 7/2004 Andrews et al.
6,835,202 B2 12/2004 Harth et al.
6,899,717 B2 5/2005 Weber et al.
7,125,542 B2 10/2006 Miller et al.
2002/0094998 A1 7/2002 Burke et al.
2002/0198174 A1 12/2002 Lyons
2003/0060763 A1 3/2003 Penfold et al.
2003/0069286 A1 4/2003 Chen et al.
2003/0095995 A1 5/2003 Wong
2003/0171320 A1 9/2003 Guyer
2003/0211123 A1 11/2003 Shukla et al.

(56) References Cited

U.S. PATENT DOCUMENTS

| | | | | |
|---|---|---|---|---|
| 2003/0225152 | A1 | 12/2003 | Andrews | |
| 2004/0054374 | A1 | 3/2004 | Weber | |
| 2004/0077562 | A1 | 4/2004 | Chandavarkar et al. | 514/36 |
| 2004/0137059 | A1 | 7/2004 | Nivagioli et al. | |
| 2004/0152664 | A1 | 8/2004 | Chang et al. | |
| 2005/0065137 | A1 | 3/2005 | Jani et al. | 514/171 |
| 2005/0101582 | A1 | 5/2005 | Lyons et al. | 514/179 |
| 2005/0181017 | A1 | 8/2005 | Hughes et al. | 424/427 |
| 2005/0244458 | A1 | 11/2005 | Huang | |
| 2005/0244461 | A1 | 11/2005 | Nivaggioli | |
| 2005/0244462 | A1 | 11/2005 | Farooq | |
| 2005/0244463 | A1 | 11/2005 | Huang | |
| 2005/0244464 | A1 | 11/2005 | Hughes et al. | |
| 2005/0244465 | A1 | 11/2005 | Nivaggioli | |
| 2005/0244466 | A1 | 11/2005 | Whitcup | |
| 2005/0244468 | A1 | 11/2005 | Huang et al. | 424/427 |
| 2005/0244470 | A1 | 11/2005 | Hughes | |
| 2005/0244471 | A1 | 11/2005 | Shiah et al. | |
| 2005/0244474 | A1 | 11/2005 | Huang et al. | |
| 2005/0244478 | A1 | 11/2005 | Hughes | |
| 2005/0244479 | A1 | 11/2005 | Huang | |
| 2005/0250737 | A1 | 11/2005 | Hughes et al. | 514/58 |
| 2006/0009498 | A1 | 1/2006 | Whitcup | 514/357 |
| 2006/0141049 | A1 | 6/2006 | Lyons et al. | |
| 2006/0173060 | A1 | 8/2006 | Chang et al. | |
| 2007/0298073 | A1 | 12/2007 | Whitcup et al. | |
| 2007/0298074 | A1 | 12/2007 | Robinson et al. | |

FOREIGN PATENT DOCUMENTS

| | | | |
|---|---|---|---|
| EP | 0 364 417 | 9/1989 | |
| EP | 0 430 539 | 6/1991 | |
| EP | 0 488 401 | 6/1992 | |
| WO | WO 95/13765 | 5/1995 | |
| WO | WO 96/38174 | 12/1996 | |
| WO | WO 00/02564 | 1/2000 | |
| WO | WO 01/30323 | 5/2001 | |
| WO | WO 01/58240 | 8/2001 | |
| WO | WO 02/02076 | 1/2002 | |
| WO | WO 02/05815 | 1/2002 | |
| WO | WO 02/43785 | 6/2002 | |
| WO | WO 02/089815 A2 | 11/2002 | A61K 31/573 |
| WO | WO 02/100437 | 12/2002 | |
| WO | WO 2004/069280 A1 | 8/2004 | A61K 47/48 |
| WO | WO 2004/073607 | 9/2004 | A61K 31/56 |
| WO | WO 2004/087043 A2 | 10/2004 | |
| WO | WO 2005/110380 | 11/2005 | |

OTHER PUBLICATIONS

Capozzi, Angelo et al, Distant Migration of Silicone Gel From a Ruptured Breast Implant, Silicone Gel Migration, 1978, 302-3, 62 (2).

Clark, D. Dick et al, The Influence of Triamcinolone Acetonide on Joint Stiffness in the Rat, The Journal of Bone and Joint Surgery, 1971, 1409-1414, 53A (7).

Cohen, Miriam et al, Organization and Adhesive Properties of the Hyaluronan Pericellular Coat of Chondrocytes and Epithelial Cells, Biophysical Journal, Sep. 2003, 1996-2005, 85.

Deland, Frank, Intrathecal Toxicity Studies with Benzyl Alcohol, Toxicology and Applied Pharmacology, 1973, 153-6, 25, Academic Press, Inc.

Geroski, Dayle et al, Drug Delivery for Posterior Segment Eye Disease, Investigative Ophthalmology & Visual Science, Apr. 2000, 961-964, 41(5).

Grecomoro, G. et al, Intra-articular treatment with sodium hyaluronate in gonarthrosis: a controlled clinical trial versus placebo, Pharmatherapeutica, 1987, 137-141, 5 (2).

Jones, Adrian et al, Intra-articular Hyaluronic Acid Compared to Intra-articular Triamcinolone Hexacetonide in Inflammatory Knee Osteoarthritis, Osteoarthritis and Cartilage, 1995, 269-273, 3.

Kopp, Sigvard et al, The Short-term Effect of Intra-articular Injections of Sodium Hyaluronate and Corticosteroid on Temporomandibular Joint Pain and Dysfunction, Journal of Oral and Maxillofacial Surgery, 1985, 429-435, 43.

Mancinelli, Laviero et al, Intramuscular High-dose Triamcinolone Acetonide in the Treatment of Severe Chronic Asthma, West J Med, 1997, 322-329, 167 (5).

McCarty, Daniel et al, Inflammatory Reaction after Intrasynovial Injection of Microcrystalline Adrenocorticosteroid Esters, Arthritis and Rheumatism, 1964, 359-367, 7 (4).

Selvi, Enrico et al, Arthritis Induced by Corticosteroid Crystals, The Journal of Rheumatology, 2004, 622, 31 (3).

Zulian, F. et al, Triamcinolone Acetonide and Hexacetonide Intra-articular Treatment of Symmetrical Joints in Juvenile Idiopathic Arthritis: A Double-blind Trial, Rheumatology, 2004, 1288-1291, 43.

Hertzberger-ten Cate R. et ai., Intra-articular steroids in pauciarticular juvenile chronic arthritis, type I, Eur J Ped 1991 150: 170-172.

Hurst, E.W., Adhesive Arachnoiditis and Vascular Blockage caused by Detergents and Other Chemical Irritants: an Experimental Study. J. Path. Bact., 1955. 70: p. 167.

Hetherington, N.J. and M.J. Dooley, Potential for patient harm from intrathecal administration of preserved solutions. Med J Aust, 2000. 173(3): p. 141.

Liao, Y-H., et al., Hyaluronan: pharmaceutical characterization and drug delivery, Drug Delivery, 12: 327-342, 2005.

Goldberg V. et al., Hyaluronans in the treatment of osteoarthritis of the knee: evidence for disease-modifying activity, Osteoarthritis & Cartilage 2005; 13: 216-224.

Pinheiro M. et ai., Adverse effect of soft tissue augmentation with hyaluronic acid, J Cosmet Dermatol. 2005; 4: 184-6.

Ioftsson T. et ai., Determination of Aqueous Solubility by Heating and Equilibration: A Technical Note, AAPS PharmSciTech. 5 2006;7(1): Article 4.001:1 0.1208/pt0701 04.

Yang J. et ai., Transdermal delivery system of triamcinolone acetonide from a gel using phonophoresis, Arch Pharm Res 29(5); 412-417: 2006.

Fokjaet et al, “Pharmaceutical Formulation Development of Peptides and Proteins”, Taylor & Francis Limited, 2000, p. 131.

Gaffney et al (Intra-articular triamcinolone hexacetonide in knee osteoarthritis: factors influencing the clinical response. Ann Rheum Dis. May 1995;54(5):379-81).

U.S. Appl. No. 60/567,339, filed Apr. 2004, Hughes.

U.S. Appl. No. 60/567,423, filed Apr. 2004, Hughes.

U.S. Appl. No. 60/587,092, filed Jul. 2004, Whitcup.

ALPHAGAN® P, Product Information.

Anderson, L.C. et al., *An Injectable Substained Release Fertility Control System, Contraception*, 1976;,13:375-384.

Aukunuru et al., *In Vitro Delivery of Nano- and Micro-Particles to Human Retinal Pigment Epithelial* (*ARPE-19*) *Cells*, Drug Delivery Technologies, 2002; 2(2):50-57.

Baker R., *Controlled Release of Biologically Active Agents*, A Wiley-Interscience Publication, 1987; 73-75.

Bito, L.Z., *Biological protection with prostaglandins*, Cohen, M.M., ed., Boca Raton, Fla., CRC Press Inc., 1985; 31-252.

Bito L.Z., *Glaucoma: Applied Pharmacology in the Medical Treatment*, Drance, S.M. and Neufled, A.H. Eds., New York, Grune & Stratton, 1984; 477-505.

Bito L.Z., *Prostaglandins: Old Concepts and New Perspectives*, Archives of Ophthalmology, 1987; 105:1036-1039.

Bodor, N. et al., *A Comparison of Intraocular Pressure Elevating Activity of Loteprednol Etabonate and Dexamethasone in Rabbits*, Current Eye Research, 1992; 11:525-530.

Brubaker, *Mechanism of Action of Bimatoprost* (*Lumigan*™), Survey of Ophthalmology, 2001; 45(Suppl 4):S347-S351.

Busse et al., *Tyrosine kinase inhibitors: rationale, mechanisms of action, and implications for drug resistance*, Seminars in Oncology, 2001; 28(suppl 16):47-55.

Charles J. et al., 67*Use of Bioerodible Polymers Impregnated with Mitomycin in Glaucoma Filtration Surgery in Rabbits*, Ophthalmology, Apr. 1991; 98(4): 503-508.

Chen et al., *Lumigan®: A Novel Drug for Glaucoma Therapy*, Optometry in Practice, 2002; 3:95-102.

(56) References Cited

OTHER PUBLICATIONS

Chiang et al., *Pharmacokinetics and Intraocular Pressure Lowering Effect of Timolol Preparation in Rabbit Eyes*, Journal of Ocular Pharmacology and Therapeutics, 1996; 12(4):471-480.
Coleman et al., *A 3-Month Randomized Controlled Trial of Bimatoprost (LUMIGAN) Versus Combined Timolol and Dorzolamide (Cosopt) in Patients with Glaucoma or Ocular Hypertension*, Ophthalmology, 2003; 110(12):2362-2368.
*Company News on Call*, "Oculex Announces Positive Clinical Results for Posurdex(R)—The First Biodegradable Ocular Implant in Clinical Trial" Copyright © 1996-2004 PR Newswire Association LLC.
Coquelet et al., *Successful Photodynamic Therapy Combined with Laser Photocoagulation in Three Eyes with Classic Subfoveal Choroidal Neovascularization Affecting Two Patients with Multifocal Choroiditis: Case Reports*, Bulletin of the Society of Belgian Ophthalmologists, 2002; 283:69-73.
Crabb et al., *Cloning of the cDNAs encoding the cellular retinaldehyde-binding protein from bovine and human retina and comparison of the protein structures*, Journal of Biological Chemistry, 1988; 263(35):18688-18692.
Di Colo G., *Controlled Drug Release From Implantable Matrices Based On Hydrophobic Polymers*, Biomaterials, 1992; 13(12):850-856.
Dunn et al., *ARPE-19, a human retinal pigment epithelial cell line with differentiated properties*, Experimental Eye Research, 1996; 62:155-169.
Epstein, David L., *Primary Open-Angle Glaucoma*, Chandler and Grant's Glaucoma, Lea & Febiger, 1986; 129-181.
Fabbro et al., *Protein tyrosine kinase inhibitors: new treatment modalitites?*, Current Opinion in Pharmacology, 2002; 2:374-381.
Fotsis et al., *The endogenous oestrogen metabolite 2-methoxyoestradiol inhibits angiogenesis and suppresses tumor growth*, Nature, 1994; 368:237.
Gilman, A.G. et al. eds., *Goodman and Gilman's: The Pharmacological Basis of Therapeutics*. 8th Edition, Pergamon Press: New York, 1990; 1447-1451.
Goel et al., *Tyrosine Kinase Inhibitors: A Clinical Perspective*, Current Oncology Reports, 2002; 4:9-19.
Guenther, Lyn C., *Optimizing Treatment with Topical Tazarotene*, American Journal of Clinical Dermatology, 2003; 4(3):197-202.
Haluska et al., *Receptor tyrosine kinase inhibitors*, Current Opinion in Investigational Drugs, 2001; 2(2):280-286.
Hamel et al., *Molecular cloning and expression of RPE65, a novel retinal pigment epithelium-specific microsomal protein that is post-transcriptionally regulated in vitro*, Journal of Biological Chemistry, 1993; 268(21):15751-15757.
Hare et al., *Efficacy and safety of memantine, an NMDA-Type Open-Channel Blocker, for reduction of retinal injury associated with experimental glaucoma in rat and monkey*, Survey of Ophthalmology, 2001; 45(Suppl 3):S284-S289.
Hashizoe, Mototane et al., *Scleral Plug of Biodegradable Polymers for Controlled Drug Release in the Vitreous*, Archives of Ophthalmology, 1994; 112:1380-1384.
Heller J., *Biodegradable Polymers in Controlled Drug Delivery*, CRC Critical Reviews in Therapeutic Drug Carrier Systems, 1987; 1(1):39-90
Heller J., *Hydrogels in Medicine and Pharmacy*, N.A. Peppes ed., CRC Press, Boca Raton, FL, 1987; 3:137-149.
Hoyng et al., *Pharmacological Therapy for Glaucoma*, Drugs, Mar. 2000; 59(3):411-434.
Hubbard et al., *Protein tyrosine kinase structure and function*, Annual Review of Biochemistry, 2000; 69:373-398.
Jackanicz et al., *Polyactic Acid as a biodegradable carrier for contraceptive steroids*, Contraception, 1973; 8(3):227-235.
Jampel H. et al, *Glaucoma Filtration Surgery in Monkeys Using 5-Fluorouridine in Polyanhydride Disks*, Archives of Ophthalmology, Mar. 1990; 108:430-435.
Kimura, Hideya et al., *A New Vitreal Drug Delivery System using an Implantable Biodegradable Polymeric Device*, Investigative Ophthalmology & Visual Science, 1994; 35:2815-2819.
Klimanskaya et al., *Derivation and comparative assessment of retinal pigment epithelium from human embryonic stem cells using transcriptomics*, Cloning and Stem Cells, 2004; 6(3):217-245.
Kompella et al., *Subconjunctival Nano- and Microparticles Sustain Retinal Delivery of Budesonide, a Corticosteroid Capable of Inhibiting VEGF Expression*, Investigative Ophthalmology and Visual Science, Mar. 2003; 44(3):1192-1201.
Kwak, H.W. and D'Amico, D.J., *Evaluation of the Retinal Toxicity and Pharmacokinetics of Dexamethasone After Intravitreal Injection*, Archives of Ophthalmology, 1992; 110:259-266.
Lai et al., *Alph-2 adrenoceptor agonist protects retinal function after acute retinal ischemic injury in the rat*, Visual Neuroscience, 2002; 19:175-185.
Lee D. et al., *Glaucoma Filtration Surgery in Rabbits Using Bioerodible Polymers and 5-Fluorouracil*, Ophthalmology, Dec. 1987; 94(12):1523-1530.
Lee D. et al, *The Use of Bioerodible Polymers and 5-Fluorouracil in Glaucoma Filtration Surgery*, Investigative Ophthalmology & Visual Science, Nov. 1988; 29(11):1692-1697.
"Lumigan®: a new ocular hypotensive agent for achieving target intraocular pressures," Acta Ophthalmologica Scandinavica, Scientific Abstracts, 2002; 80(4):457.
"Lumigan found effective in early phase 3", Ocular Surgery News, Mar. 2001; 19(5):1,35.
Marks R., *Topical Tazarotene: Review and Re-Evaluation*, Retinoids, 2001; 17(3):72-74.
Maurice, D.M., *Micropharmaceutics of the Eye*, Ocular Inflammation Therapy, 1983; 1:97-102.
McGhee et al., *Locally Administered Ocular Corticosteroids Benefits and Risks*; Drug Safety, 2002; 25(1):33-55.
Miller et al., *Degradation rates of oral resorbable implants (polyactates and polyglycolates) rate modification with changes in PLA/PGA copolymer ratios*, Journal of Biomedical Materials Research, 1977; 11:711-719.
Miller et al., *Synthesis and structure-activity profiles of A-Homoestranes, the Estratopones*, Journal of Medical Chemistry, 1997; 40:3836-3841.
Morita Y., et al., *Intravitreous delivery of dexamethasone sodium m-sulfobenzoate from poly (DL-lactic acid) implants*, Biological and Pharmaceutical Bulletin, Feb. 1998; 21(2): 188-90.
Nauck, M., et al., *Corticosteroids inhibit the expression of the vascular endothelial growth factor gene in human vascular smooth muscle cells*, European Journal of Pharmacology, 1998; 341:309-315.
Olsen, T.W. et al., *Human Scleral Permeability: Effects of Age, Cryotherapy, Transscleral Diode Laser, and Surgical Thinning*, Investigative Ophthalmology & Visual Science, 1995; 36(9):1893-1903.
Phillips et al., *Efficacy of 0.1% Tazarotene cream for the treatment of photodamage*, Archives of Dermatology, Nov. 2002; 138(11):1486-1493.
Phillips et al., *Penetration of timolol eye drops into human aqueous humour: the first hour*, British Journal of Ophthalmology, 1985; 69:217-218.
*Physician's Desk Reference*, product information on "Alphagan®P", 54 Edition, 2000; 494-494.
*Physician's Desk Reference for Ophthalmic Medicines*, 30 Edition, 2002; 285.
Pribluda et al., *2-Methoxyestradiol: an endogenous antiangiogenic and antiproliferative drug candidate*, Cancer and Metastasis Reviews, 2000; 19:173-179.
Quigley et al., *The mechanism of optic nerve damage in experimental acute intraocular pressure elevation*, Investigative Ophthalmology & Visual Science, 1980; 19:505.
Rao et al., *Preparation and Evaluation of Ocular Inserts Containing Norfloxacin*, Turkish Journal of Medical Science, 2004; 34:239-246.
Rao, N.A. et al., *Introcular Inflammation and Uveitis*, In Basic and Clinical Science Course, San Francisco: American Academy of Ophthalmology, 1997-1998; section 9, 5780, 102-103, 152-156.

(56) References Cited

OTHER PUBLICATIONS

Rechtman et al., *Intravitreal triaminolone with photodynamic therapy for subfoveal choroidal neovascularisation in age related macular degeneration*, British Journal of Ophthalmology, 2004; 88:344-347.
Renfro, L. et al., *Ocular Effects of Topical and Systemic Steroids*, Dermatologic Clinics, 1992; 10:505-512.
Rogojina et al., *Comparing the use of Affymetrix to spotted oligonucleotide microarrays using two retinal pigment epithelium cell lines*, Molecular Vision, 2003; 9:482-496.
Schuettauf et al., *Effects of anti-glaucoma medications on ganglion cell survival: the DBA/2J mouse model*, Vision Research, 2002; 42(20):2333-2337.
Schumacher et al., *The physiological estrogen metabolite 2-methoxyestradiol reduced tumor growth and induces apoptosis in human solid tumors*, Journal of Cancer Research and Clinical Oncology, 2001; 127:405-410.
Schwartz, B., *The Response of Ocular Pressure to Corticosteroids*, Ophthalmology Clinics of North America; 1966; 6:929-989.
Siebold et al., Prodrug 5, 3 (1989).
Skalka, H.W. et al., *Effect of Corticosteroids on Cataract Formation*, Archives of Ophthalmology, 1980; 98:1773-1777.
Smith et al., *Sustained-release subconjunctival 5-fluorouracil*, Ophthalmic Surgery and Laser, Sep. 1996; 27(9):763-767.
Starr, M.S., *Further Studies on the Effect of Prostaglandin on Intraocular Pressure in the Rabbit*, Experimental Eye Research, 1971; 11:170-177.
Streilein et al., *Ocular immune privilege: therapeutic opportunities from an experiment of nature*, Nature Reviews Immunology, 2003; 3:879-889.
Survey of Ophthalmology 2002; 47(3); 295.
Tan, D.T.H. et al., *Randomized Clinical Trial of a New Dexamethasone Delivery System (Surodex) for Treating of Post-Cataract Surgery Inflammation*, Ophthalmology, 1999; 106(2):223-231.
"Tazarotene", *Drugs Future*, 2003; 28(2):208-209. Annual Update 2003: Dermatologic Drugs.
Tracy et al., *Factors affecting the degradation rate of poly (lactide-co-glycolide) Microspheres in vivo and in vitro*, Biomaterials, 1999; 20:1057-1062.
United States Pharmacopeia, The National Formulary; USP 23/NF 18; 1995; pp. 1790-1798.
Watson et al., *A Six-month, Randomized, Double-masked Study Comparing Latanoprost with Timolol in Open-angle Glaucoma and Ocular Hypertension*, Ophthalmology, 1996; 103:126-137.
Wheeler, *Experimental studies of agents with potential neuroprotective properties*, Acta Ophthalmologica Scandinavica, 1999; 77(229):27-28.
Wheeler et al, *Role of Alpha-2 Agonists in Neuroprotection*, Survey of Ophthalmology, Apr. 2003; 48(Suppl 1):S47-S51.
WoldeMussie, *Neuroprotection of retinal ganglion cells in experimental models of glaucoma*, Minerva Oftalmol, 2000; 42(2):71-78.
WoldeMussie et al., *Neuroprotective effects of memantine in different retinal injury models in rats*, Journal of Glaucoma, 2002; 11(6):474-480.
Woodward et al., *AGN 2024 (Lumigan®): A Synthetic Prostamide Analog that Lowers Primate Intraocular Pressure by Virtue of Its Inherent Pharmacological Activity*, ARVO 2002; (CD-ROM):POS.
Woodward et al., "The Pharmacology of Bimatoprost (Lumigan™)", Survey of Ophthalmology, 2001; 45(Suppl 4): S337-S345.
Yeung et al., *Cytotoxicity of Triamcinolone on Cultured Human Retinal Pigment Epithelial Cells: Comparison with Dexamethasone and Hydrocortisone*, Japanese Journal of Ophthalmology, 2004; 48:236-242.
Zhou, T. et al., *Development of a Multiple-Drug Delivery Implant for Introcular Management of Proliferative Vitreoretinopathy*, Journal of Controlled Release, 1998; 55:281-295.
Antcliff R., et al Marshall J., *The pathogenesis of edema in diabetic maculopathy*, Semin Ophthalmol 1999; 14:223-232.
Armaly M., *Statistical attributes of the steroid hypertensive response in the clinically normal eye*, Invest Ophthalmol Vis Sci 1965; 4:187-197.
Audren, F. et al., *Pharmacokinetic-Pharmacodynamic modeling of the effect of Triamcinolone Acetonide on Central Macular Thickness in Patients with Diabetic Macular Edema*, Inv Ophth & Vis Sci, 45(10); 3435-3441: Oct. 2004.
Becker B,. *Intraocular pressure response to topical corticosteroid*, Invest Ophthalmol Vis Sci 1965; 4:198-205.
Beer P. et al., *Intraocular concentration and pharmacokinetics of triamcinolone acetonide after a single intravitreal injection*, Opthal 110(4); 681-686: Apr. 2003.
Butcher J. et al., Bilateral cataracts and glaucoma induced by long term use of steroid eye drops. BMJ 1994; 309-343.
Challa J. et al., *Exudative macular degeneration and intravitreal triamcinolone: 18 month follow up*, Aust NZ J Ophthalmol 1998; 26:277-281.
Chang H. et al., *Development of a topical suspension containing three active ingredient*, Drug Dev and Ind Pharm, 28(1), 29-39 (2002).
Cheng, Cheng-Kuo et al., *Intravitreal Sustained-Release Dexamethasone Device in the Treatment of Experimental Uveitis*, Investigative Ophthalmology & Visual Science, Feb. 1995, vol. 36, No. 2, pp. 442-453.
Danis R. et al., *Intravitreal triamcinolone acetonide in exudative age-related macular degeneration*, Retina 2000; 20:244-250.
Dea I. et al., *Hyaluronic acid: a novel, double helical molecule*, Science, Feb. 9, 1973;179(73):560-2.
Edelman et al., *Corticosteroids inhibit VEGF-induced vascular leakage in a rabbit model of blood-retinal and blood-aqueous barrier breakdown*, Exp Eye Res Feb. 2005;80(2):249-58.
Einmahl S. et al, *Evaluation of a novel biomaterial in the suprachoroidal space of the rabbit eye*, Invest Ophthal & Vis Sci 43(5); 1533-1539 (2002).
Einmahl S. et al, *Therapeutic applications of viscous and injectable poly(ortho esters)*, Adv Drug Del Rev 53 (2001) 45-73.
Enyedi, Laura et al., *An Intravitreal Device Providing Sustained Release of Cyclosporine and Dexamethason*, Current Eye Research (1995) pp. 549-557.
Hainsworth, Dean P. et al., *Sustained Release Intravitreal Dexamethasone*, Journal of Ocular Pharmacology and Therapeutics, (1996) vol. 12, No. 1, pp. 57-63.
Helliwell P., *Use of an objective measure of articular stiffness to record changes in finger joints after intra-articular injection of corticosteroid*, Ann Rheum Dis 1997;56:71-73.
Inoue M. et al., *Vitreous concentrations of triamcinolone acetonide in human eyes after intravitreal or subtenon injection*, Am J Opth 138(6); 1046-1048: 2004.
Jonas J. et al., *Intraocular injection of crystalline cortisone as adjunctive treatment of diabetic macular edema*, Am J Ophthalmol 2001; 132:425-427.
Jonas J. et al., *Intravitreal injection of crystalline cortisone as adjunctive treatment of proliferative vitreoretinopathy*, Br J Ophthalmol 2000; 84:1064-1067.
Jonas J. et al., *Intravitreal injection of triamcinolone for diffuse diabetic macular edema*, Arch Ophthalmol 2003; 121:57-61.
Kochinke, F. et al., *Biodegradable Drug Delivery System for Uveitis Treatment*, Investigative Ophthalmology & Visual Science, Feb. 15, 1996, vol. 37. No. 3, 186-B98.
Martidis A. et al., *Intravitreal triamcinolone for refractory diabetic macular edema*, Ophthalmology 2002; 109:920-927.
McCarty D., et al., *Inflammatory reaction after intrasynovial injection of microcrystalline adrenocorticosteroid esters*, Arthritis and Rheumatism, 7(4); 359-367 (1964).
McCuen B. et al., *The lack of toxicity of intravitreally administered triamcinolone acetonide*, Am J Ophthalmol 1981; 91:785-788.
Nauck M. et al., *Corticosteroids inhibit the expression of the vascular endothelial growth factor gene in human vascular smooth muscle cells*, Euro J Pharmacol 1998; 341:309-315.

(56) References Cited

OTHER PUBLICATIONS

Nauck M. et al., *Induction of vascular endothelial growth factor by platelet-activating factor and platelet-derived growth factor is downregulated by corticosteroids*, Am J Resp Cell Mol Biol 1997; 16:398-406.

Nishimura A. et al., *Isolating Triamcinolone acetonide particles for intravitreal use with a porous membrane filter*, Retina, vol. 23(6); 777-779 (2003).

Pe'er J. et al., *Vascular endothelial growth factor upregulation in human central retinal vein occlusion*, Ophthalmology 1998; 105:412-416.

Penfold P. et al., *Exudative macular degeneration and intravitreal triamcinolone: A pilot study*, Aust NZ J Ophthalmol 1995; 23:293-298.

Roth D. et al., *Noninfectious endophthalmitis associated with intravitreal triamcinolone injection*, Arch Opthalmol 2003; 121: 1279-1282.

Schindler R. et al., *The clearance of intravitreal triamcinolone acetonide*, Am J Ophthalmol 1982; 93:415-417.

Scholes G. et al., *Clearance of triamcinolone from vitreous*, Arch Ophthalmol 1985; 103:1567-1569.

Sutter F. et al., *Pseudo-endophthalmitis after intravitreal injection of triamcinolone*, Br J Ophthalmol 2003; 87:972-974.

PERIPHERALLY ADMINISTERED VISCOUS FORMULATIONS

CROSS REFERENCE

This application is divisional application of application Ser. No. 11/828,561, filed Jul. 26, 2007, which is a continuation in part of application Ser. No. 11/741,366, filed Apr. 27, 2007, which is a continuation in part of application Ser. No. 11/354,415, filed Feb. 14, 2006, which is a continuation in part of application Ser. No. 10/966,764, filed Oct. 14, 2004, which application claims the benefit of provisional patent application Ser. No. 60/519,237, filed Nov. 12, 2003 and provisional patent application Ser. No. 60/530,062, filed Dec. 16, 2003, all of which applications are hereby incorporated herein by reference in their entireties.

BACKGROUND

The present invention relates to viscous formulations and to methods for treating and/or preventing various peripheral diseases and conditions by peripheral administration to a patient of a viscous formulation. Peripheral administration includes intradermal, subdermal, subcutaneous, intramuscular, intra-articular (i.e. to treat an articular pathology such as a knee or facet joint osteoarthritis) and epidural (i.e. to treat a radiculopathy, spondylitis, and spondylosis [also known as degenerative disc disease, spinal arthritis, osteoarthritis of the spine]) routes of administration. The administration can be carried out, for example, by injection, insertion or implantation of the viscous formulation. In particular the present invention relates to extended release and sustained release viscous formulations, including injectable implants, for treating various non-ophthalmic inflammatory and/or painful conditions, such as skin or joint pain and/or inflammation, radicular pain from nerve root irritation or inflammation, or chronic back pain from spondylosis or spondylitis.

A pharmaceutical composition (synonymously a formulation or a composition) is a formulation which contains at least one active ingredient (for example an anti-inflammatory polymer such as a polymeric hyaluronic acid and/or a corticosteroid such as a triamcinolone) as well as, for example, one or more excipients, buffers, carriers, stabilizers, preservatives and/or bulking agents, and is suitable for administration to a patient to achieve a desired effect or result. The pharmaceutical compositions disclosed herein can have diagnostic, therapeutic, cosmetic and/or research utility in various species, such as for example in human patients or subjects.

Therapeutic use of a hyaluronic acid or of a corticosteroid is known. Thus, hyaluronic acid (also called hyaluronan and sodium hyaluronate) formulations for both therapeutic and cosmetic use are known. Hyaluronic acid is most frequently referred to as hyaluronan due to the fact that it exists in vivo as a polyanion and not in the protonated acid form. U.S. Pat. Nos. 4,636,524; 4,713,448; 5,099,013, and 5,143,724 disclose particular hyaluronans or hyaluronic acids and methods for making them. Additionally, intra-articular use of a hyaluronic acid (i.e. as a viscosupplement) or of an anti-inflammatory steroid is known. See e.g. Kopp S. et al., *The short-term effect of intra-articular injections of sodium hyaluronate and corticosteroid on temporomandibular joint pain and dysfunction*, J Oral Maxillofac Surg 1985 June; 43(6):429-35; Grecomoro G., et al., *Intra-articular treatment with sodium hyaluronate in gonarthrosis: a controlled clinical trial versus placebo*, Pharmatherapeutica. 1987; 5(2):137-41; Adams M., *An analysis of clinical studies of the use of crosslinked hyaluronan, hylan, in the treatment of osteoarthritis*, J Rheumatol Suppl. 1993 August; 39:16-8, and; Jones, A. et al., *Intra-articular hyaluronic acid compared to intra-articular triamcinolone hexacetonide in inflammatory knee osteoarthritis*, Osteoarthritis Cartilage. 1995 December; 3(4):269-73

Commercially available hyaluronic acid formulations include Juvederm™ (Allergan), an injectable dermal filler comprised of a cross-linked hyaluronic acid. Also known are Orthovisc® (Anika), Durolane (Smith & Nephew), Hyalgan® (Sanofi), Hylastan® (Genzyme), Supartz® (Seikagaku/Smith & Nephew)), Synvisc® (Genzyme), Euflexxa®, (Ferring) which are used as injectable (intra-articular) hyaluronic acid viscosupplements, of various molecular weights with various degrees of cross-linking of the hyaluronic acid, for treating osteoarthritis joint pain.

Compositions for therapeutic or cosmetic use comprising a high molecular weight hyaluronic acid and one or more active agents has been disclosed. See e.g. U.S. patent application Ser. Nos. 11/039,192; 11/695,527; 11/742,350; 10/966,764; 11/354,415, and; 11/741,366.

Certain corticosteroids (such as triamcinolone) can have anti-inflammatory properties. Thus, intra-articular corticosteroids have been used to treat various joint diseases. See e.g. Zulian F., et al., *Triamcinolone acetonide and hexacetonide intra-articular treatment of symmetrical joints in juvenile idiopathic arthritis: a double-blind trial*, Rheum 2004; 43:1288-1291. (use of 2 mg to 80 mg of triamcinolone acetonide) and; Hertzberger-ten Cate R. et al., *Intra-articular steroids in pauciarticular juvenile chronic arthritis*, type I, Eur J Ped 1991; 150: 170-172 (intra-articular 20 mg triamcinolone used to treat juvenile arthritis). Triamcinolone has been used to treat joint stiffness (Clark D. et al., *The influence of triamcinolone acetonide on joint stiffness in the rat*, J Bone Joint Surg Am 1971; 53:1409-144).

Additionally, intramuscular steroids have been given to treat acute conditions, until the patient can be managed by use of oral steroids, such as asthma (Mancinelli L. et al., *Intramuscular high-dose triamcinolone acetonide in the treatment of severe chronic asthma*, West J Med November 1997:167 (5); 322-329 [up to 360 mg of the triamcinolone was administered daily for three days to a patient]). Subcutaneous and intradermal administration of a steroid is not a preferred route of administration because dermal atrophy can result. When administered by intramuscular injection the risk of dermal atrophy by the steroid can be reduced by giving the injection in a deep gluteal muscle area and avoiding leakage of the steroid formulation into the dermis.

Unfortunately, there are significant drawbacks and deficiencies with known viscous formulations and with known corticosteroid formulations for peripheral use. For example, multiple (five or more) peripheral administrations of a hyaluronic acid can be required to treat a peripheral condition. Additionally, an aqueous corticosteroid formulation of triamcinolone can quickly clear (diffuse out of and/or is removed by one or more active transport mechanisms) from the site of peripheral administration. Rapid clearance can necessitate frequent re-administration (re-dosing) in order to provide an effective treatment. Additionally, therapeutic corticosteroids due to their low water solubility are typically administered as an aqueous suspension of relatively large, irregularly shaped crystals (particles). Such steroid particles can induce an inflammatory response upon administration. This may occur because macrophages present at the administration site can be unable to remove the steroid particles (by phagocytosis) which have a large morphology and irregular geometry. Indeed such particles can be toxic to macrophages and lead to cell death. The death of macrophages then leads to release of pro-inflammatory cytokines that cause both acute and chronic inflammation. Clinical examples of toxicity from particles include gouty arthritis, where urate crystals that range from 5 to 20 microns can cause arthritis. See eg. Helliwell P, *Use of an objective measure of articular stiffness to record changes in finger joints after intra-articular injection of corticosteroid*, Ann Rheum Dis 1997; 56: 71-73 (intra-articular corticosteroid injection can cause crystal synovitis).

Thus, it is known that macrophages are injured when phagocytosing urate crystals leading to an inflammatory response. Notably, patients treated with medication that reduces macrophage activity, such as colchicine, have a dramatic improvement in their arthritis. Another clinical example of joint deposition of large, irregularly shaped crystals that are injurious to macrophages is pseudo-gout. Here, joint inflammation is caused by deposition of calcium pyrophosphate dehydrate in patients that have hyperparathyroidism. An example of joint inflammation related to injected drug particles is crystal-induced synovitis, where 1-2% of patients that receive intra-articular injections of Lederspan, Kenalog, or other corticosteroid depot formulations, develop a post-injection exacerbation of the joint inflammation. (McCarty D., et al., *Inflammatory reaction after intrasynovial injection of microcrystalline adrenocorticosteroid esters*, Arthritis and Rheumatism, 7(4); 359-367 (1964) (intra-articular injection of corticosteroids crystals can cause sterile inflammation also referred to as post-injection flare). See also Selvi E. et al., *Arthritis induced by corticosteroid crystals*, J Rheumatology 2004; 31: 3 (osteoarthritis patient treated with intra-articular injection of 40 mg triamcinolone hexacetonide developed acute arthritis induced by the injected triamcinolone crystals). The particles in these formulations, which are on the average over 10 microns and have irregular morphology, are very similar to the urate crystals in joint of patients with gout or pseudo-gout.

A triamcinolone pharmaceutical composition available under the trade name Kenalog® (Bristol-Myers-Squibb, Princeton N.J.) has been used to treat various conditions by intramuscular or intra-articular (intrabursal use) administration. Each milliliter (ml) of Kenalog® 40 composition comprises 40 milligrams (mg) of triamcinolone acetonide, sodium chloride as a tonicity agent, 10 mg (0.99%) benzyl alcohol as a preservative, 7.5 mg (0.75%) of carboxymethylcellulose sodium and 0.4 mg (0.04%) of polysorbate 80 as resuspension aids. Benzyl alcohol preservative and/or polysorbate 80 can potentially be toxic to sensitive tissues. Thus, preservative-containing corticosteroid formulations have been linked to cases of adhesive arachnoiditis following epidural injections exacerbating a patient's back pain. See e.g. Hurst, E. W., *Adhesive Arachnoiditis and Vascular Blockage caused by Detergents and Other Chemical Irritants: an Experimental Study*. J. Path. Bact., 1955. 70: p. 167; DeLand, F. H., *Intrathecal toxicity studies with benzyl alcohol*. Toxicol Appl Pharmacol, 1973. 25(2): p. 153, and; Hetherington, N. J. and M. J. Dooley, *Potential for patient harm from intrathecal administration of preserved solutions*. Med J Aust, 2000. 173(3): p. 141.

Significantly, the triamcinolone acetonide in Kenalog® rapidly separates and precipitates from the remainder of the formulation. For example, if Kenalog® is left standing for as short a time as about five to ten minutes a substantial separation of a triamcinolone acetonide precipitate from the remainder of the composition occurs. Unfortunately, such rapid settling of the triamcinolone also occurs with other known saline based suspensions of triamcinolone (with or with preservatives and stabilizers). A substantially uniform suspension (which is not provided by Kenalog or other saline based suspensions of triamcinolone) would be beneficial to provide a consistent and accurate dose upon administration of the suspension. In addition, resuspension processing requires the use of the resuspension aids noted above which can affect sensitive tissues.

Additionally, administration of known formulations of a corticosteroid, such as triamcinolone can also result in an allergic or inflammatory reaction possibly due to the burst or high release rates of triamcinolone from the known formulations. As noted above such a reaction can also be due to or be exacerbated due to the large and irregular size of the insoluble corticosteroid particles administered.

Thus, there is a need for a formulation for peripheral administration to treat a peripheral condition which will not have the undesirable characteristics of: presence of toxic preservatives or surfactants in the formulation; rapid release of most or all of the active agent, and that will have a longer period of residence of the active agent at the site of peripheral administration and well as comprising a non or low immunogenic formulation.

DRAWINGS

FIG. 1 is a flow chart which summarizes a preferred manufacturing process for making the triamcinolone formulations of Examples 1 to 9.

Figure 2:
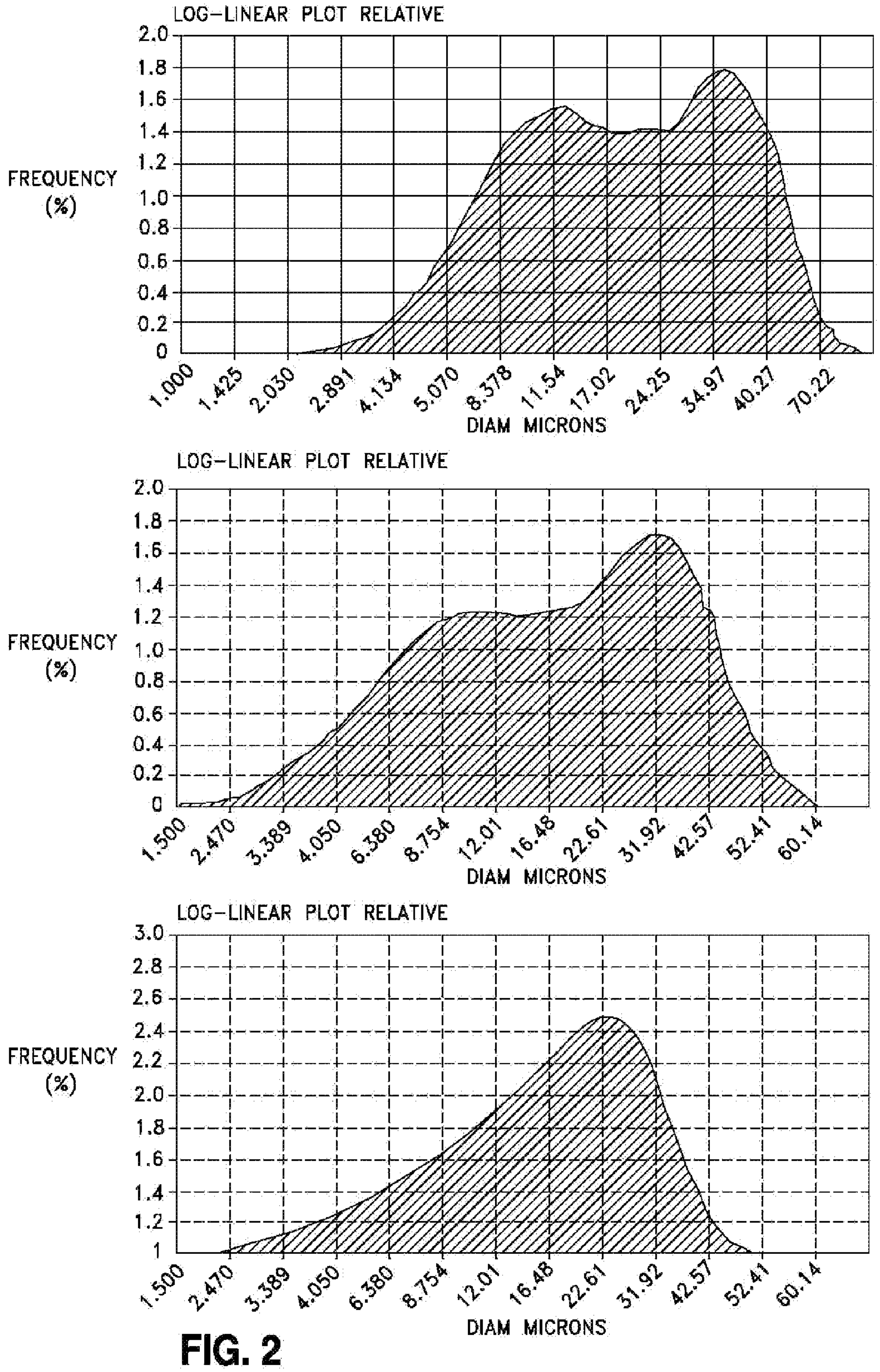
Figure 3A:
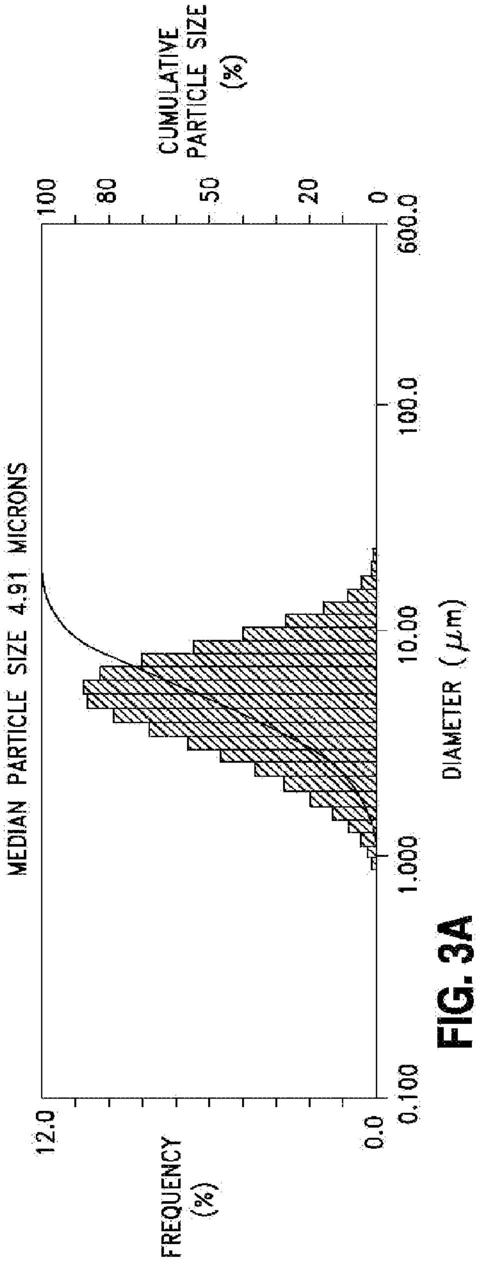
Figure 3B:
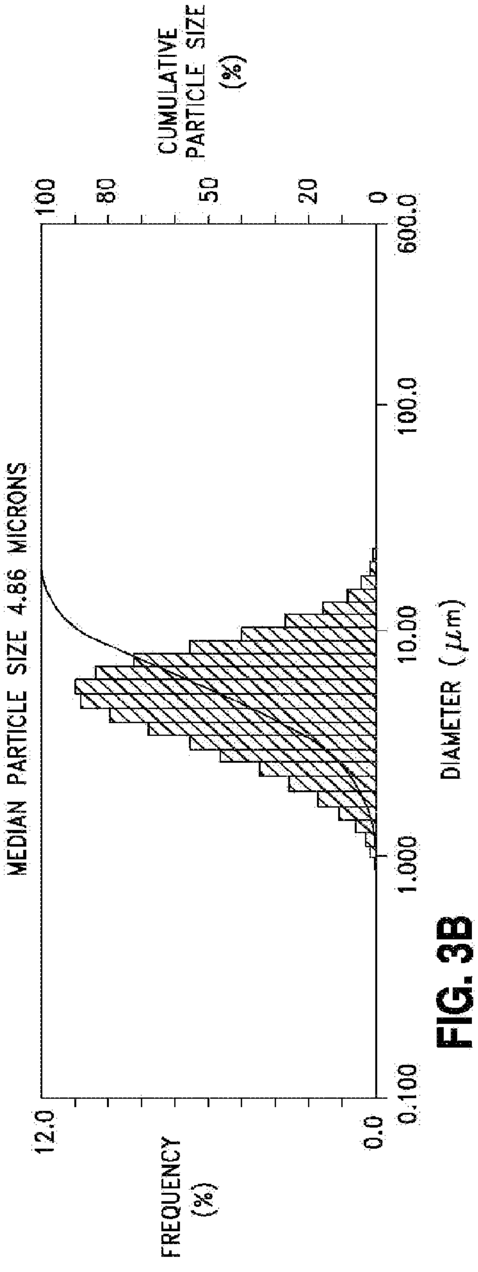
Figure 3C:
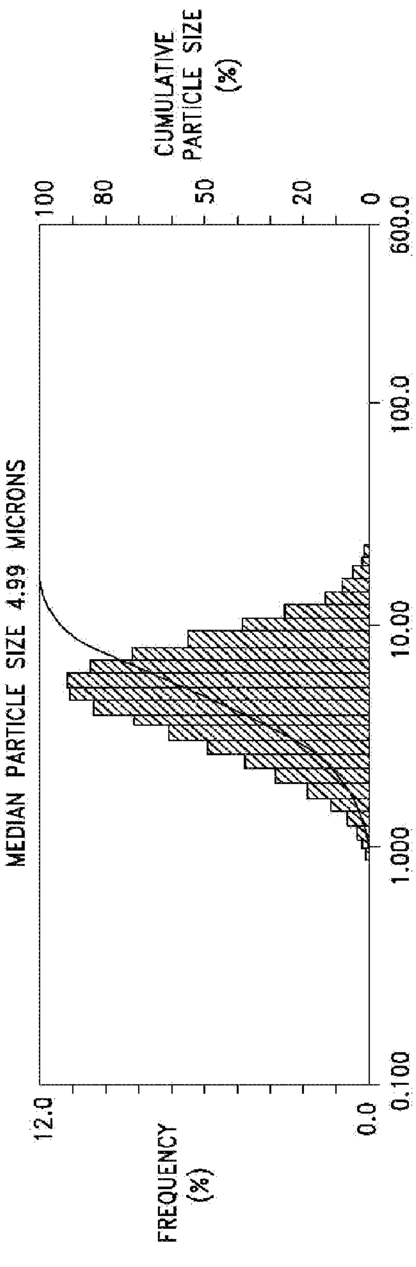
Figure 3D:
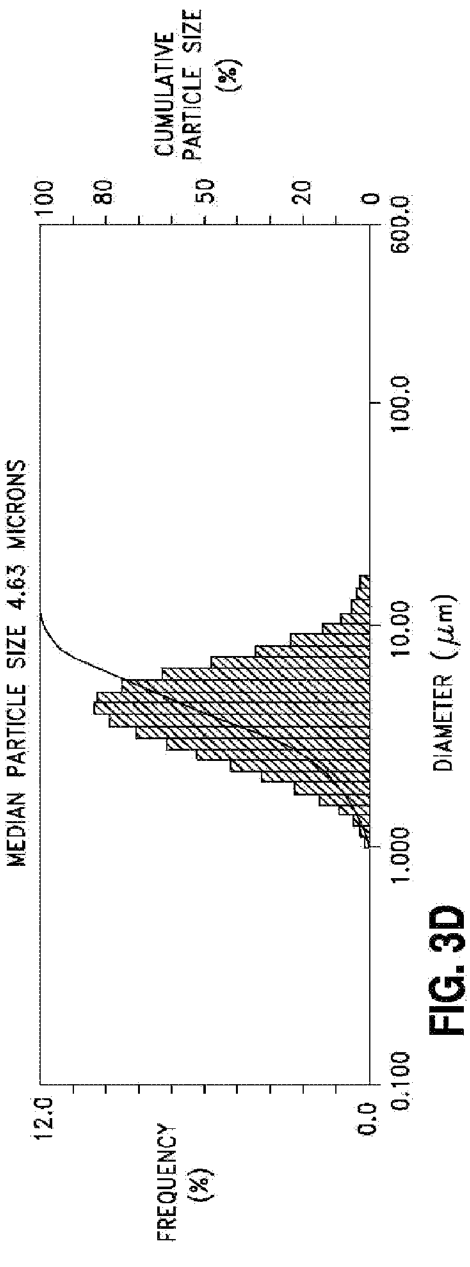

FIG. 2 consists of three graphs showing the size (diameter) in microns (x-axis) of triamcinolone acetonide particles in three commercial lots of Kenalog-40 vs the frequency of occurrence of the measured particles diameters. Triamcinolone acetonide particle size diameter and distribution was determined by laser light scattering using a Horiba LA 300 instrument.

FIG. 3 consists of four bar graphs (A, B, C and D) showing the size (diameter) in microns (x-axis) of the triamcinolone acetonide particles raw material used to make the Trivaris formulations disclosed herein formulation vs the frequency of occurrence of the measured particles diameters. The line graph in FIGS. 3A to 3D shows the area under the curve for cummulative (%) triamcinolone acetonide particle size (right hand side y axis). Triamcinolone acetonide particle size diameter and distribution was determined by laser light scattering using a Horiba LA 300 instrument.

SUMMARY

The present invention provides viscous formulations and methods for treating and/or preventing various peripheral conditions by peripheral administration to a patient of a viscous formulation. Peripheral administration includes intradermal, subdermal, subcutaneous, intramuscular, intra-articular (i.e. to treat an articular pathology such as knee or facet joint osteoarthritis), and epidural (i.e. to treat a radiculopathy, spondylitis, and spondylosis [a.k.a. degenerative disc disease, spinal arthritis, osteoarthritis of the spine]), routes of administration. The peripheral administration can be carried out, for example, by injection, insertion or implantation of the viscous formulation. In particular the present invention relates to extended release and sustained release viscous formulations, including injectable implants, for treating various non-ophthalmic inflammatory and/or painful conditions, such as skin or joint pain and/or inflammation, radicular pain from nerve root irritation or inflammation, or chronic back pain from spondylosis or spondylitis.

Additionally, the present invention provides sterile, preservative-free, sustained release viscous formulations for treating peripheral conditions with the desirable characteristics of low immunogenicity, lack of toxic preservatives or surfactants in the formulation, and sustained release the active agent.

DEFINITIONS

As used herein, the words or terms set forth below have the following definitions.

"About" means that the item, parameter or term so qualified encompasses a range of plus or minus ten percent above and below the value of the stated item, parameter or term.

"Administration" or "to administer" means the step of giving (i.e. administering) a pharmaceutical composition to a subject. The pharmaceutical compositions disclosed herein can be "locally administered", that is administered at or in the vicinity of the site at which a therapeutic result or outcome is desired. For example to treat an peripheral condition by peripheral administration of a viscous formulation. "Sustained release" means release of an active agent (such as a corticosteroid and/or an anti-inflammatory hyaluronic acid) over a period of about seven days or more, while "extended release" means release of an active agent over a period of time of less than about seven days.

"Entirely free (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Peripheral administration" means the step of administering a viscous formulation by a route of administration which is not an intraocular administration and which is also not an immediate systemic administration (such as an intravenous administration or oral ingestion) of the viscous formulation. Thus, peripheral administration excludes intravenous and oral administrations but includes, for example, subdermal, intradermal, subcutaneous, intramuscular and intra-articular routes of administration.

"Peripheral condition" means a non-ophthalmic disease or condition, such as a dermatologic, articular, allergic, inflammatory and/or painful disease or condition, such as an arthritic condition. Examples of peripheral conditions that can be treated by peripheral intramuscular or intra-articular administration include allergies, asthma, dermatitis, drug hypersensitivity reactions, rhinitis, serum sickness, transfusion reactions, dermatologic conditions, bullous dermatitis herpetiformis, exfoliative erythroderma, mycosis fungoides, pemphigus, severe erythema multiforme (Stevens-Johnson syndrome), endocrine disorders, drenocortical insufficiency, adrenal hyperplasia, hypercalcemia, thyroiditis, enteritis, colitis, anemia, aplasia, thrombocytopenia, trichinosis, meningitis, leukemia, lymphomas, multiple sclerosis, cerebral edema, craniotomy, head injury, proteinuria, nephrotic syndrome, lupus erythematosus, beryllıosis, tuberculosis, pneumonia, sarcoidosis, arthritis (all types), carditis, spondylitis, dermatomyositis, polymyositis, systemic lupus erythematosus, bursitis, tenosynovitis and epicondylitis.

"Peripheral location" means a location on or within the periphery of a mammalian body. Thus a peripheral locations includes locations on or within the skin, a voluntary (striated) muscle, such as on or within an arm or leg, within a joint (intra-articular) and all anatomical areas near and within the vertebral column. Intraocular and visceral (that is within the gut, gut cavity, viscera, internal organs, GI, GU, etc system) are not peripheral locations.

"Pharmaceutical composition" means a formulation in which an active ingredient (the active agent) can be an anti-inflammatory polymer (such as a polymeric hyaluronic acid) and/or a steroid, such as a corticosteroid, such as a triamcinolone. The word "formulation" means that there is at least one additional ingredient in the pharmaceutical composition besides the active agent. A pharmaceutical composition is therefore a formulation which is suitable for diagnostic or therapeutic administration (i.e. by peripheral injection or by insertion of a depot or implant) to a subject, such as a human patient.

"Substantially free" means present at a level of less than one percent by weight of the pharmaceutical composition.

"Sustained release" means release of an active agent (such as a triamcinolone) over a period of about seven days or more, while "extended release" means release of an active agent over a period of time of less than about seven days.

All the viscosity values set forth herein were determined at 25° C. (unless another temperature is specified). Additionally, all the viscosity values set forth herein were determined at a shear rate of about 0.1/second (unless another shear rate is specified).

The present compositions are highly suitable for peripheral administration to a peripheral location. The present compositions are advantageously substantially free of added preservative components, for example, contain no benzyl alcohol preservative. In addition, the present compositions advantageously require no resuspension aid or aids. Overall, the present compositions are easily and effectively injectable into a peripheral location of a patient's body and can be maintained as a substantially uniform suspension for long periods of time, for example, at least about one week or more, without resuspension processing, for example, without requiring shaking or other agitating of the composition to obtain substantial suspension uniformity. In short, the present compositions and methods provide substantial enhancements and advantages, for example, relative to the prior art Kenalog® 40 composition and methods of using such prior art composition.

In one broad aspect of the present invention, compositions useful for injection into a peripheral location are provided. Such compositions can comprise a corticosteroid component, a viscosity inducing component, and an aqueous carrier component. The corticosteroid component is present in a therapeutically effective amount. The corticosteroid component can be present in the compositions in a plurality of particles.

The present compositions can include a corticosteroid component in an amount of up to about 25% (w/v) or more of the composition. In one very useful embodiment, the corticosteroid component is present in an amount of at least about 80 mg/ml of composition. Preferably, the corticosteroid component is present in an amount in a range of about 1% to about 10% or about 20% (w/v) of the composition.

In one very useful embodiment, the corticosteroid component comprises triamcinolone acetonide. The viscosity inducing component is present in an amount effective in increasing the viscosity of the composition. Any suitable, preferably ophthalmically acceptable, viscosity inducing component may be employed in accordance with the present invention. Advantageously, the viscosity inducing component is present in an amount in a range of about 0.5% to about 20% (w/v) of the composition. In one particularly useful embodiment, the viscosity inducing component is a hyaluronic acid polymer component, such as sodium hyaluronate.

The preferred Hyaluronic acid ("HA") used in the formulations disclosed as the preferred viscosity inducing component has the following characteristics. First, the HA provides an increase in viscosity but has a high shear rate, meaning that it retains syringeability through 25-30 gauge needles. Second, the HA is a natural component of the extracellular matrix of many mammalian tissues therefore providing a biocompatible viscosity inducing component. Third, the HA is a tissue adhesive so that when HA is injected into a tissue such as a muscle diffusion and migration of the HA through fascial planes in minimized. See e.g. Cohen et al. Biophys J. 2003; 85: 1996-2005. A poorly adhesive polymer such as silicone can migrate through tissues. See e.g. Capozzi et al. Plast Reconstr Surg. 1978; 62:302-3. The tissue adhesion and therefore low tissue migration characteristic of a formulation which comprises HA enables the formulation to remain largely at the injection site. Thus a corticosteroid-HA formulation will have the advantageous characteristic of low diffusion out of the peripheral location, such as an intra-articular location (i.e. to treat facet joint arthritis). Additionally, a botulinum toxin-HA formulation will have the advantageous characteristic of low diffusion out of the peripheral location, such as an intramuscular location (i.e. into the small orbicularis muscle to treat hemifacial spasm). Hence, use of HA in a formulation can limit drug or biologic exposure to surrounding or adjacent non-target tissues, thereby limiting side effects (with regard to para-ocular botulinum toxin administration) such as ptosis or visual impairment.

Third, in order to have drug released from a carrier or the active agent (i.e. steroid crystals) solubilized contact with water is required. The preferred HA used provides this through an ability to become hydrated (absorb water).

Fourth, the HA used is a polymer that can be cross-linked to varying degrees, thereby permitting alteration of characteristics such as rate of HA migration for the peripheral location of administration, rate of active agent diffusion and migration out of the HA carrier.

In one embodiment, the present compositions have a viscosity of at least about 10 cps or at least about 100 cps, preferably at least about 1,000 cps, more preferably at least about 10,000 cps and still more preferably at least about 70,000 cps, for example, up to about 250,000 cps, or about 300,000 cps, at a shear rate of 0.1/second. The present compositions are structured or have make-ups so as to be injectable into a peripheral location of a human or animal body preferably through a 27 gauge needle, more preferably through a 29 or 30 gauge needle.

Without wishing to limit the invention to any particular theory of operation, it is believed that the use of relatively high viscosity compositions, as described herein, provides for effective, and preferably substantially uniform, suspension of the steroid component particles injectable into a peripheral location.

In one embodiment of the invention, the corticosteroid component is present in a plurality of particles which are substantially uniformly suspended in the composition and remain substantially uniformly suspended in the composition for at least about 1 week, preferably at least about 2 weeks or at least about 1 month, and still more preferably at least about 6 months or at least about 1 year or at least about 2 years, without requiring resuspension processing, that is, without requiring being shaken or otherwise agitated to maintain the corticosteroid component particles substantially uniformly suspended in the composition.

Compositions having such substantially uniform suspension of corticosteroid component particles, so as to be able to provide a consistent and accurate dose upon administration, provide substantial advantages relative to the prior art. In particular, the present compositions may be manufactured, shipped and stored for substantial periods of time without the corticosteroid component particles precipitating from the remainder of the composition. Having the corticosteroid component particles maintained substantially uniformly suspended in the composition allows the composition to provide long term dosing consistency and accuracy per unit dose amount administered, without any need to resuspend the corticosteroid particles.

The aqueous carrier component is advantageously biocompatible and may include one or more conventional expedients. For example, the carrier component may include an effective amount of at least one of a preservative component, a tonicity component and a buffer component. In one advantageous embodiment, the present compositions include no added preservative component. This feature reduces or minimizes or even substantially eliminates adverse reactions upon administration which may be caused by or linked to the presence of a preservative component. Although a resuspension component may be employed in accordance with the present invention, in many instances, because of the ability of the present composition to remain a substantially uniform suspension for a long period of time without requiring resuspension processing, the compositions advantageously contain no added resuspension components.

Methods of treating a peripheral condition are disclosed and are included within the scope of the present invention. In general, such methods comprise administering, e.g. injecting a corticosteroid component-containing composition, for example, a composition in accordance with the present intention to a peripheral location. Such administering is effective in providing a desired therapeutic effect. The administering step advantageously comprises at least one of intramuscular or intra-articular injecting.

Our invention encompasses a pharmaceutical composition for treating a peripheral condition. The composition can comprise a triamcinolone present in a therapeutically effective amount as a plurality of particles; a viscosity inducing component in an amount effective to increase the viscosity of the composition, and; an aqueous carrier component. The composition can have a viscosity of at least about 10 cps at a shear rate of about 0.1/second and is injectable into a peripheral location, for example through a 27 gauge needle. By reducing the viscosity of our formulation it can be injected into the peripheral through a 28, 29 or 30 gauge needle.

Preferably, the triamcinolone particles of the pharmaceutical composition are substantially uniformly suspended in the composition and the viscosity inducing component is a polymeric hyaluronate.

A detailed embodiment within the scope of our invention is a pharmaceutical composition for treating a peripheral condition, comprising triamcinolone particles; polymeric hyaluronate, in which the triamcinolone particles are suspended; sodium chloride; sodium phosphate, and water. The pharmaceutical composition can have a viscosity at a shear rate of about 0.1/second of between about 80,000 cps to about 300,000, preferably from about 100,000 cps to about 300,000 cps, and most preferably from about 1280,000 cps to about 225,000 cps. Note that the pharmaceutical composition can have a viscosity at a shear rate of about 0.1/second of between about 80,000 cps and about 300,000 cps, and that when the pharmaceutical composition has a viscosity at a shear rate of about 0.1/second of between about 100,000 cps and about 150,000 cps it can be injected into a peripheral location through a 27, 28, 29 or 30 gauge needle. We have found that even with a 300,000 cps our formulations can be injected through a 30 gauge needle due to shear thinning once the formulation is in movement in the syringe. The sodium phosphate present in the pharmaceutical composition can comprise both monobasic sodium phosphate and dibasic sodium phosphate. Additionally, the pharmaceutical composition can comprise between about 2% w/v triamcinolone and about 8% w/v triamcinolone, between about 2% w/v hyaluronate and about 3% w/v hyaluronate, about 0.6% w/v sodium chloride and about 0.03% w/v sodium phosphate to about 0.04% w/v sodium phosphate. Alternately, the pharmaceutical composition of claim 5 can comprise between about 0.5% w/v hyaluronate and about 6% w/v hyaluronate. If desired the hyaluronate can be heated (see Example 11) to decrease its molecular weight (and therefore its viscosity) in the formulation.

The pharmaceutical composition can also comprises between about 0.6% w/v sodium chloride to about 0.9% w/v sodium chloride. Generally, more sodium chloride is used in the formulation as less phosphate is used in the formulation, for example 0.9% sodium chloride can be used if no phosphate is present in the formulation, as in this manner the tonicity of the formulation can be adjusted to obtain the desired isotonicity with physiological fluid. The pharmaceutical composition can comprise between about 0.0% w/v sodium phosphate and 0.1% w/v sodium phosphate. As noted, more phosphate can be used in the formulation if less sodium chloride is present in the formulation so as to obtain a desired pH 7.4 buffering effect.

A more detailed embodiment within the scope of our invention is a pharmaceutical composition for treating a peripheral condition, the pharmaceutical composition consisting essentially of triamcinolone particles, polymeric hyaluronate, in which polymeric hyaluronate the triamcinolone particles are suspended, sodium chloride, sodium phosphate, and water. The pharmaceutical composition can have a viscosity at a shear rate 0.1/second at 25° C. of between about 128,000 cps and about 225,000 cps and the sodium phosphate present in the pharmaceutical composition can be present as both monobasic sodium phosphate and dibasic sodium phosphate. The most preferable viscosity range is 140,000 to 280,000 cps at a shear rate 0.1/second at 25° C.

A further embodiment of our invention is a triamcinolone suspension for treating a peripheral condition, consisting of triamcinolone particles, polymeric hyaluronate, in which the triamcinolone particles are suspended, sodium chloride, dibasic sodium phosphate heptahydrate, monobasic sodium phosphate monohydrate, and water, wherein the composition has a viscosity at a shear rate 0.1/second of between about 128,000 cps and about 225,000 cps.

Our invention also includes a method for treating a peripheral condition by administering (as by injecting) the pharmaceutical composition set forth above to the peripheral of a human or animal, thereby treating the peripheral condition. Thus we have invented a method for treating a peripheral condition edema by administering to a peripheral location pharmaceutical composition comprising a triamcinolone, and a hyaluronate, wherein the pharmaceutical composition having a viscosity at a shear rate 0.1/second of between about 128,000 cps and about 225,000 cps.

A pharmaceutical composition within the scope of our invention for treating a peripheral condition can comprise a triamcinolone present in a therapeutically effective amount as a plurality of particles, a viscosity inducing component in an amount effective to increase the viscosity of the composition, and an aqueous carrier component, wherein the composition has a viscosity of at least about 10 cps at a shear rate of 0.1/second and is injectable into a peripheral location and wherein the pharmaceutical composition releases the triamcinolone with substantially first order release kinetics over a period of at least about 45 days after the peripheral injection or administration. This pharmaceutical composition can exhibit reduced generation of inflammation, no plume effect (that is no wide dispersion of the triamcinolone into the peripheral as soon as the triamcinolone is injected), and cohesiveness (as shown by the retention of the form of the triamcinolone gel for 30 weeks or longer after peripheral injection of the triamcinolone gel formulation) upon peripheral injection of the pharmaceutical composition.

Our invention encompasses a method for treating a peripheral condition, the method comprising the step of peripheral administration of a sustained release pharmaceutical composition implant comprising a triamcinolone present in a therapeutically effective amount as a plurality of particles, a viscosity inducing component in an amount effective to increase the viscosity of the composition, and an aqueous carrier component, wherein the composition has a viscosity of at least about 10 cps at a shear rate of 0.1/second and is injectable into a peripheral location, and wherein the peripheral condition is treated for up to about 30 weeks by the triamcinolone released from the viscous formulation. In this method the pharmaceutical composition can comprise triamcinolone particles, polymeric hyaluronate, in which the triamcinolone particles are suspended, sodium chloride, sodium phosphate, and water. Additionally, the peripheral administration can be injected through a 27 gauge needle into the peripheral location, and in an aggregate number of patients practise of the method results in less peripheral inflammation than does practise of the same method with a second pharmaceutical composition which is a saline solution or suspension of a triamcinolone.

Our invention also includes a process for making a pharmaceutical composition by (a) mixing triamcinolone particles about 4 microns to about 8 microns in diameter with sodium chloride crystals, and about 35% to about 40% of the total volume of the water (water for injection) used to make the formulation; (b) heating the triamcinolone and sodium chloride mixture to a temperature between about 120° C. and about 140° C., thereby preparing a first part; (c) mixing a sodium phosphate and water, thereby preparing a second part; (d) dissolving sodium hyaluronate with a molecular weight between about 1.0 million Daltons and about 1.9 million Daltons in another about 35% to about 40% of the total water volume used to make the formulation, followed by sterile filtration after the dissolving; (e) lyophilization of the dissolved sodium hyaluronate; (f) reconstitution of the lyophilized, sterile sodium hyaluronate, thereby preparing a third part; and; (g) aseptically combining the first, second and third parts, thereby making a sterile, uniform triamcinolone pharmaceutical composition which is, an opaque white gel suspension suitable for peripheral injection to treat an peripheral condition. Water is added as needed (q.s.) to make the desired gel suspension which is about 80% to about 90% by weight water.

Also within the scope of our invention is a pharmaceutical composition for treating a peripheral condition, the pharmaceutical composition comprising a plurality of corticosteroid particles mixed with a viscous polymer, wherein the pharmaceutical composition has a viscosity of between about 130,000 cps and about 300,000 cps at a shear rate of about 0.1/second at about 25° C., and the pharmaceutical composition can be injected into a peripheral location through a 25 to 33 gauge needle. The corticosteroid particles can have a substantially uniform diameter, as shown for example by FIGS. 3A, 3B, 3C and 3D. Additionally, preferably substantially all (i.e. up to 90-97%) of the corticosteroid particles are embedded within the viscous polymer. The corticosteroid can be a triamcinolone and the viscous polymer can be a polymeric hyaluronate or a polymeric hyaluronic acid.

An alternate method for treating a peripheral condition can comprise the step of injecting into a peripheral location of a patient with a peripheral condition a viscous pharmaceutical composition comprising a plurality of corticosteroid particles mixed into a viscous polymeric matrix, wherein the pharmaceutical composition has a viscosity of between about 130,000 cps and about 300,000 cps at a shear rate of about 0.1/second at about 25° C., such that about one hour after the peripheral injection only about 10% or less (or only about 5% or less or only about 3% or less) of the corticosteroid particles are present in the peripheral free of the polymeric matrix.

An alternate process for making an pharmaceutical composition for peripheral administration can comprise the step of mixing an aqueous suspension of a plurality of corticosteroid particles and an aqueous solution of a viscous polymeric matrix, so that the resulting pharmaceutical composition has a viscosity of between about 130,000 cps and about 300,000 cps at a shear rate of about 0.1/second at about 25° C. The corticosteroid particles can have a median particle size of between about 4 microns and about 5 microns. By use of this process for making a pharmaceutical composition the corticosteroid particles can have a stable diameter for at least three months after the pharmaceutical has been made and stored for three months in a syringe placed horizontally at about 25° C. at about 60% relative humidity.

Our invention also includes a pharmaceutical composition for treating an articular pathology, the pharmaceutical composition comprising a plurality of corticosteroid particles mixed with a viscous polymer, wherein the pharmaceutical composition has a viscosity of between about 130,000 cps and about 300,000 cps at a shear rate of about 0.1/second at about 25° C.

Our invention also includes a method for treating an articular pathology, the method comprising the step of injecting into a joint of a patient with an articular pathology (such as a joint or spine inflammation) a viscous pharmaceutical composition comprising a plurality of corticosteroid particles mixed into a viscous polymeric matrix, wherein the pharmaceutical composition has a viscosity of between about 130,000 cps and about 300,000 cps at a shear rate of about 0.1/second at about 25° C.

Our invention includes a method for treating a peripheral condition, the method comprising the step of administering to a peripheral location of a human body a viscous formulation comprising a viscous polymer, wherein the viscous formulation has a viscosity of between about 130,000 cps and about 300,000 cps at a shear rate of about 0.1/second at about 25° C., thereby treating at least one symptom of the peripheral condition. The peripheral condition can be an articular pathology. The peripheral location can be an intra-articular location. The step of administering can be carried out by injecting. The viscous formulation can comprises a plurality of corticosteroid particles mixed with the viscous polymer. The corticosteroid can be a triamcinolone. The viscous polymer can be a polymeric hyaluronate or a polymeric hyaluronic acid.

Our invention also include a method for treating a peripheral condition, the method comprising the step of injecting into a peripheral location of a patient with a peripheral condition a viscous formulation comprising a plurality of corticosteroid particles mixed into a viscous polymeric matrix, wherein the pharmaceutical composition has a viscosity of between about 130,000 cps and about 300,000 cps at a shear rate of about 0.1/second at about 25° C., such that about one hour after the peripheral injection only about 10% or less of the corticosteroid particles are present at the peripheral location free of the polymeric matrix. About one hour after the peripheral injection only about 3-5% or less of the corticosteroid particles can be present at the peripheral location free of the polymeric matrix.

Our invention also includes a method for treating arthritis, the method comprising the step of injecting into a joint of a patient with arthritis a viscous formulation comprising a plurality of corticosteroid particles mixed into a viscous polymeric matrix, wherein the viscous formulation has a viscosity of between about 130,000 cps and about 300,000 cps at a shear rate of about 0.1/second at about 25° C.

Our invention also includes a method for treating a peripheral condition, the method comprising the steps of (a) administering to a peripheral location of a human body a viscous formulation comprising a viscous polymer, wherein the viscous formulation has a viscosity of between about 130,000 cps and about 300,000 cps at a shear rate of about 0.1/second at about 25° C., thereby treating at least one symptom of the peripheral condition, and; (b) administering to a peripheral location of a human body a plurality of corticosteroid particles, thereby treating at least one symptom of the peripheral condition. The plurality of corticosteroid particles can be mixed with the viscous polymer.

Finally, our invention includes a method for treating a peripheral condition of a patient selected from the group of peripheral conditions consisting of osteoarthritis, radiculopathy, spondylitis, and spondylosis, the method comprising the step of injecting into a peripheral location of the a viscous formulation comprising a plurality of corticosteroid particles mixed into a viscous polymeric matrix, wherein the pharmaceutical composition has a viscosity of between about 130,000 cps and about 300,000 cps at a shear rate of about 0.1/second at about 25° C.

DESCRIPTION

The present invention is based upon our discovery of viscous formulations specifically designed for peripheral injection to treat various peripheral conditions. Our viscous formulations have numerous superior characteristics and advantages, including the following when the viscous formulation is a viscous steroid formulation: (1) the steroid present in our formulations does not rapidly settle out from or precipitate from the formulations. Importantly our formulations have a shelf life of at least two years, meaning that our formulations can be left standing for up to about two years before peripheral administration, and after two years the formulation can still provide a consistent and accurate dose of the steroid upon peripheral injection to the formulation; (2) our formulations are free of preservatives and resuspension aids, such as benzyl alcohol and/or a polysorbate; (3) concomitantly, our formulations have a much reduced inflammatory and toxicity effect; (4) as well as being sterile and preservative-free our viscous steroid formulations can provide sustained release of therapeutic amounts of the steroid over multi-month periods upon peripheral injection of such formulations. Thus, our viscous suspension steroid formulations are sustained release implants; (5) peripheral administration of our viscous formulations is not associated with an increased incidence of adverse events such as inflammation; (6) our viscous formulations permit steroid particles (crystals) to be released (as they solubilize) from a discrete unitary location, thereby avoiding a plume effect (rapid dispersion) characteristic of aqueous steroid formulations upon administration, and; (7) the sustained release characteristic of our formulations reduces the need for peripheral administration of large drug quantities to achieve a desired therapeutic effect.

Generally, the present invention provides viscous formulations useful for peripheral administration to a human or animal to treat a peripheral condition. An important aspect of our invention is the finding that upon a peripheral administration a rapid dispersion of the steroid particles can be reduced by formulating the steroid with a polymer that increases the formulation viscosity and that causes the steroid particles to agglomeration after the peripheral administration. This advantageously decreases steroid particle exposure to the tissues and reduces the inflammatory response. Post-injection inflammation is also reduced by eliminating form the formulation preservatives, such as benzyl alcohol, that have been shown to cause local tissue toxicity and inflammation.

Where an active agent used is a formulation disclosed herein a triamcinolone, the triamcinolone used is preferably a triamcinolone acetonide because of the superior therapeutic properties of triamcinolone acetonide as compared to other forms of triamcinolone.

Specifically, we have determined that post-injection joint inflammation associated with intra-articular application of a corticosteroid formulation can be decreased by: (1) reducing the particle size of the corticosteroid to ≤10 microns with the morphology of the particle preferably being uniform or substantially; (2) adding a polymer to increase the viscosity of the corticosteroid formulation to reduce steroid particle dispersion within the joint, and (3) limiting the use of preservatives in the formulation.

A preferred formulation for treating an articular (joints) condition can be a viscous formulation comprises of particles of a steroid (such as triamcinolone acetonide) which have a median particle size of <10 microns and a substantially uniform shape. The steroid particles are mixed with a hyaluronic acid, a preferred polymer due to its anti-inflammatory properties. (Dea I., et al., *Hyaluronic acid: a novel, double helical molecule*, Science. 1973 Feb. 9; 179(73):560-2. (hyaluronic is a polysaccharide double helix which can inhibit lymphocytes). See also Liao, Y-H., et al., *Hyaluronan: pharmaceutical characterization and drug delivery*, Drug Delivery, 12: 327-342; 2005. Hyaluronic acid is naturally found in high concentrations in the synovial fluid and serves as a joint lubricant, shock absorber, and it reduces friction between the articular surfaces. In addition, hyaluronic acid supplementation into the joint synovium has a chondroprotective affect through multiple mechanisms and has been found to be disease-modifying as well as a symptom-modifying in patients with osteoarthritis. (Goldberg V. et al., *Hyaluronans in the treatment of osteoarthritis of the knee: evidence for disease-modifying activity*, Osteoarthritis & Cartilage 2005; 13: 216-224) (intra-articular hyaluronic acid may both relieve and treat osteoarthritis).

Our invention includes a viscous formulation which can be used as a single dose application and which is preservative-free and which does not cause post-injection aseptic endophthalmitis, a condition analogous to crystal-induced synovitis. Our viscous formulations have an optimal steroid particle size, a hyaluronic acid component, and no preservatives and can be use to treat peripheral conditions such as rheumatoid arthritis and osteoarthritis, and spinal conditions such as facet arthritis, and patients requiring epidural or spinal root injections for chronic pain.

Our viscous formulations can also be used as dermal fillers. Hyaluronic acid has been injected into facial tissue to smooth out wrinkles and folds, especially around the nose, mouth (nasolabial folds), and forehead (glabellar folds). Hyaluronic acid has also used for increasing dermal volume to improve the appearance of scars that may be related to trauma or acne. Reduced lip and earlobe volume occurring with age can be improved with injections of hyaluronic acid. Chin and cheek augmentation can be effectively accomplished with local injections of hyaluronic acid. Unfortunately, facial soft-tissue volume replacement using hyaluronic acid, including that produced from non-animal sources, have been associated with post-injection inflammatory responses. (Pinheiro M. et al., *Adverse effect of soft tissue augmentation with hyaluronic acid*, J Cosmet Dermatol. 2005; 4: 184-6) (patient developed erythematous-edematous facial lesion after subcutaneous injection of a hyaluronic acid as a facial dermal filler, which was treated with local triamcinolone in saline injections). Post-injection inflammatory responses include acute local hypersensitivity reactions and local granulomatous reactions that can respond to local application of corticosteroids. It is known that low concentrations (less than 1 wt %) of a steroid (such as triamcinolone) when given as an intradermal application can be useful to locally treat inflammatory conditions of the skin, such as discoid lupus erythematosus and psoriatic plaques. Our invention includes a combination of low concentrations of a steroid with a hyaluronic acid to reduce post-injection inflammation.

Another benefit of our viscous formulations is that upon intramuscular administration the viscous component of the formulation reduces or prevents leakage of the steroid into the adjacent dermis.

Although our viscous formulations are not administered in a manner which provides an immediate systemic administration they can be does in a manner which permits a slow or controlled entry of the active agent into the systemic system of the patient. For this purpose generally from 2.5 mg to 100 mg per day of the active agent steroid can be administered within the viscous formulation, depending on the disease or condition being treated. Thus, an initial dose can be of about 40 to 80 mg of a steroid in the viscous formulation injected deeply into a gluteal muscle (thereby preventing atrophy of subcutaneous fat). The equivalent milligram dosage of various glucocorticoids is cortisone 25, triamcinolone 4, hydrocortisone 20, paramethasone 2, prednisolone 5, betamethasone 0.75, prednisone 5, dexamethasone 0.75 and methylprednisolone 4.

When our formulation is administration by intra-articular injection 2.5 to 5 mg of the steroid can be used for smaller joints and from 5 to 15 mg for larger joints, depending on the specific disease entity being treated. For adults, doses up to 10 mg for smaller areas and up to 40 mg for larger areas have usually been sufficient. Single injections into several joints, up to a total of 80 mg can be given. The number of required injections can be reduced from 5 to 2. Thus, the patient gets receive less steroid overall since can use lower (2% instead of 8 wt %) steroid followed by use of HA, for same or better anti-inflammatory effect. Additionally, use of micronized particles of corticosteroids, <10 microns, and preferably <5 microns, are less injurious to macrophages, and have the potential for less inflammation.

Compositions within the scope of our invention can comprise a corticosteroid component; a viscosity inducing component; and an aqueous carrier component. The compositions are advantageously biocompatible. The present viscous formulations are advantageously substantially free of added preservative components. In addition, the present viscous formulations preferably include no added resuspension component, such as polysorbate-80, which is included in the Kenalog®-40 composition.

The viscous formulations can include a corticosteroid component. Such corticosteroid component is present in the compositions in a therapeutically effective amount, that is in an amount effective in providing a desired therapeutic effect. The corticosteroid component is present in the composition in a plurality of particles. Any suitable corticosteroid component may be employed in according to the present invention. Such corticosteroid component advantageously has a limited solubility in water, for example, at 25° C. For example, the corticosteroid component preferably has a solubility in water at 25° C. of less than 10 mg/ml. One particularly useful characteristic of the presently useful corticosteroid components is the ability of such component to reduce inflammation.

Examples of useful corticosteroid components include, without limitation, cortisone, prednesolone, triamcinolone, triamcinolone acetonide, fluorometholone, dexamethosone, medrysone, loteprednol, derivatives thereof and mixtures thereof. As used herein, the term "derivative" refers to any substance which is sufficiently structurally similar to the material of which it is identified as a derivative so as to have substantially similar functionality or activity, for example, therapeutic effectiveness, as the material when the substance is used in place of the material. In one very useful embodiment, the corticosteroid component comprises triamcinolone acetonide.

The corticosteroid component advantageously is present in an amount of at least about 10 mg per ml of the composition. One important advantage of the present invention is the effective ability of the present compositions to include relatively large amounts or concentrations of the corticosteroid component. Thus, the corticosteroid component may be present in the present compositions in an amount in the range of about 1% or less to about 5% or about 10% or about 20% or about 30% or more (w/v) of the composition. Providing relatively high concentrations or amounts of corticosteroid component in the present compositions is beneficial in that reduced amounts (volumes for injection) of the composition may be required to be placed or injected into a peripheral location in order to provide the same amount or more corticosteroid component relative to compositions, such as Kenalog®-40, which include less than 4% (w/v) of the corticosteroid component. Thus, in one very useful embodiment, the present compositions include more than about 4% (w/v), for example at least about 5% (w/v), to about 10% (w/v) or about 20% (w/v) or about 30% (w/v) of the corticosteroid component. For example, about 50 μL of our Example 8 or 9 formulation provide respectively 2 mg and 4 mg of triamcinolone. This is in contrast to other formulations (such as Kenalog 40) which require 100 μL to provide 4 mg of triamcinolone.

The viscosity inducing component is present in an effective amount in increasing, advantageously substantially increasing, the viscosity of the composition. Without wishing to limit the invention to any particular theory of operation, it is believed that increasing the viscosity of the compositions to values well in excess of the viscosity of water, for example, at least about 100 cps at a shear rate of 0.1/second at 25 degrees C, compositions which are highly effective. The relatively high viscosity of the present compositions are believed to enhance the ability of the present compositions to maintain the corticosteroid component particles in substantially uniform suspension in the compositions for prolonged periods of time, for example, for as long as 1 to 2 years, without requiring resuspension processing. The relatively high viscosity of the present compositions may also have an additional benefit of at least assisting the compositions to have the ability to have an increased amount or concentration of the corticosteroid component, as discussed elsewhere herein, for example, while maintaining such corticosteroid component in substantially uniform suspension for prolonged periods of time.

Advantageously, the present compositions have viscosities of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. The present compositions not only have the relatively high viscosity as noted above but also have the ability or are structured or made up so as to be effectively placeable, e.g., injectable preferably through a 27 gauge needle, or even through a 30 gauge needle.

The presently useful viscosity inducing components preferably are shear thinning components in that as the present composition containing such a shear thinning viscosity inducing component is injected through a narrow space, such as 27 gauge needle, under high shear conditions the viscosity of the composition is substantially reduced during such passage. After such passage, the composition regains substantially its pre-injection viscosity so as to maintain the corticosteroid component particles in suspension.

Any suitable viscosity inducing component, for example, biocompatible viscosity inducing component, may be employed in accordance with the present invention. The viscosity inducing component is present in an amount effective in providing the desired viscosity to the composition. Advantageously, the viscosity inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and the like factors, such as shear thinning. The viscosity inducing component is chosen to provide at least one advantage, and preferably multiple advantages, to the present compositions, for example, in terms of each of injectability into a peripheral location viscosity, sustainability of the corticosteroid component particles in suspension, for example, in substantially uniform suspension, for a prolonged period of time without resuspension processing, bio compatibility with tissues into which the composition is to be placed and the like advantages. The viscosity inducing component preferably comprises a polymeric component and/or at least one viscoelastic agent.

Examples of useful viscosity inducing components include, but are not limited to, hyaluronic acid (such as a polymeric hyaluronic acid), carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures and copolymers thereof.

The molecular weight of the presently useful viscosity inducing components may be in a range of about 10,000 Daltons or less to about 2 million Daltons or more. In one particularly useful embodiment, the molecular weight of the viscosity inducing component is in a range of about 100,000 Daltons or about 200,000 Daltons to about 1 million Daltons or about 1.5 million Daltons. Again, the molecular weight of the viscosity inducing component useful in accordance with the present invention, may vary over a substantial range based on the type of viscosity inducing component employed, and the desired final viscosity of the present composition in question, as well as, possibly one or more other factors.

In one very useful embodiment, a viscosity inducing component is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component (i.e. a polymeric hyaluronic acid) preferably is in a range of about 50,000 Daltons or about 100,000 Daltons to about 1.3 million Daltons or about 2 million Daltons. In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation rate to the extent that often no resuspension processing is necessary over the estimated shelf life, for example, at least about 2 years, of the composition. Such a composition may be marketed in pre-filled syringes since the gel cannot be easily removed by a needle and syringe from a bulk container. Pre-filled syringes have the advantages of convenience for the injector and the safety which results from less handling.

The aqueous carrier component is advantageously ophthalmically acceptable and may include one or more conventional excipients useful in ophthalmic compositions. The present compositions preferably include a major amount of liquid water. The present compositions may be, and are preferably, sterile, for example, prior to being administered.

The present compositions preferably include at least one buffer component in an amount effective to control the pH of the composition and/or at least one tonicity component in an amount effective to control the tonicity or osmolality of the compositions. More preferably, the present compositions include both a buffer component and a tonicity component.

The buffer component and tonicity component may be chosen from those which are conventional and well known in the art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, mannitol and other sugar alcohols, and other suitable ophthalmically acceptably tonicity component and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The present compositions may include one or more other components in amounts effective to provide one or more useful properties and/or benefits to the present compositions. For example, although the present compositions may be substantially free of added preservative components, in other embodiments, the present compositions include effective amounts of preservative components, preferably such components which are more compatible with or friendly to tissues into which the composition is placed than benzyl alcohol. Examples of such preservative components include, without limitation, benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

In addition, the present composition may include an effective amount of resuspension component effective to facilitate the suspension or resuspension of the corticosteroid component particles in the present compositions. As noted above, in certain embodiments, the present compositions are free of added resuspension components. In other embodiments of the present compositions effective amounts of resuspension components are employed, for example, to provide an added degree of insurance that the corticosteroid component particles remain in suspension, as desired and/or can be relatively easily resuspended in the present compositions, such resuspension be desired. Advantageously, the resuspension component employed in accordance with the present invention, if any, is chosen to be more compatible with or friendly to the tissues into which the composition is placed than polysorbate 80.

Any suitable resuspension component may be employed in accordance with the present invention. Examples of such resuspension components include, without limitation, surfactants such as poloxanes, for example, sold under the trademark Pluronic®; tyloxapol; sarcosinates; polyethoxylated castor oils, other surfactants and the like and mixtures thereof.

One very useful class of resuspension components are those selected from vitamin derivatives. Although such materials have been previously suggested for use as surfactants in compositions, they have been found to be effective in the present compositions as resuspension components. Examples of useful vitamin derivatives include, without limitation, Vitamin E tocopheryl polyethylene glycol succinates, such as Vitamin E tocopheryl polyethylene glycol 1000 succinate (Vitamin E TPGS). Other useful vitamin derivatives include, again without limitation, Vitamin E tocopheryl polyethylene glycol succinamides, such as Vitamin E tocopheryl polyethylene glycol 1000 succinamide (Vitamin E TPGSA) wherein the ester bond between polyethylene glycol and succinic acid is replaced by an amide group.

The presently useful resuspension components are present, if at all, in the compositions in accordance with the present invention in an amount effective to facilitate suspending the particles in the present compositions, for example, during manufacture of the compositions or thereafter. The specific amount of resuspension component employed may vary over a wide range depending, for example, on the specific resuspension component being employed, the specific composition in which the resuspension component is being employed and the like factors. Suitable concentrations of the resuspension component, if any, in the present compositions are often in a range of about 0.01% to about 5%, for example, about 0.02% or about 0.05% to about 1.0% (w/v) of the composition.

The availability of minimally soluble corticosteroid components, such as triamcinolone acetonide, to peripheral tissues may be limited by the dissolution rate for these substances. Slow dissolution is both good and bad for the patient. On the one hand, after a single peripheral injection of the present composition, the mean elimination half-life for triamcinolone acetonide is advantageously quite long, for example, about 19 days in nonvitrectonized patients and measurable drug levels are detected for up to about 3 months. On the other hand, therapeutic drug levels in the peripheral location may not be achieved for about 1 to about 3 days, due to the slow dissolution rate of the corticosteroid component particles.

In one embodiment of the present invention, an effective amount of a solubilizing component is provided in the composition to solubilize a minor amount, that is less than 50%, for example in a range of 1% or about 5% to about 10% or about 20% of the corticosteroid component. For example, the inclusion of a cyclodextrin component, such as β-cyclodextrin, sulfo-butylether β-cyclodextrin (SBE), other cyclodextrins and the like and mixtures thereof, at about 0.5 to about 5.0% (w/v) solubilizes about 1 to about 10% of the initial dose of triamcinolone acetonide. This presolubilized fraction provides a readily bioavailable loading dose, thereby avoiding any delay time in therapeutic effectiveness.

The use of such a solubilizing component is advantageous to provide any relatively quick release of the corticosteroid component into the peripheral location for therapeutic effectiveness. Such solubilizing component, of course, should be biocompatible acceptable or at least sufficiently compatible with the tissues into which the composition is placed to avoid undue damage to the tissue.

The pharmacokinetics of the corticosteroid component, for example, triamcinolone acetonide, following peripheral administration may involve both the rate of drug dissolution and the rate of drug efflux via the anterior route. For example, following a single peripheral injection of a composition containing 4% (w/v) of triamcinolone acetonide, triamcinolone acetonide concentration peaks (monitored in aqueous humor) after several days at thousands of nanograms per mL. This peak ($C_{max}$) is followed by a rapid decrease lasting about 200 hours, and ends in a slow elimination phase with a half-life of about 19 days. Patients typically require repeat dosing, for example about every three months.

In one embodiment of the present invention, the compositions further contain sustained release components, for example, polymers (in the form for example of gels and microspheres), such as poly (D,L,-lactide) or poly(D,L-lactide co-glycolide), in amounts effective to reduce local diffusion rates and/or corticosteroid particle dissolution rates. The result is a flatter elimination rate profile with a lower $C_{max}$ and a more prolonged therapeutic window, thereby extending the time between required injections for many patients.

Any suitable, preferably conditionally acceptable, release component may be employed. Useful examples are set forth above. The sustained release component is preferably biodegradable or bioabsorbable so that no residue remains over the long term. The amount of the delayed release component included may very over a relatively wide range depending, for example, on the specific sustained release component is being employed, the specific release profile desired and the like factors. Typical amounts of delayed release components, if any, included in the present compositions are in a range of about 0.05 to 0.1 to about 0.5 or about 1 or more percent (w/v) (weight of the ingredient in the total volume of the composition) of the composition.

The present compositions can be prepared using suitable blending/processing techniques or techniques, for example, one or more conventional blending techniques. The preparation processing should be chosen to provide the present compositions in forms which are useful for placement or injection into a peripheral location of humans or animals. In one useful embodiment a concentration corticosteroid component dispersion is made by combining the corticosteroid component with water, and the excipient (other than the viscosity inducing component) to be included in the final composition. The ingredients are mixed to disperse the corticosteroid component and then autoclaved. Alternatively, the steroid powder may be γ-irradiated before addition to the sterile carrier. The viscosity inducing component may be purchased sterile or sterilized by conventional processing, for example, by filtering a dilute solution followed by lyophylization to yield a sterile powder. The sterile viscosity inducing component is combined with water to make an aqueous concentrate. Under aseptic conditions, the concentrated corticosteroid component dispersion can be blended or mixed and added or combined as a slurry to the viscosity inducing component concentrate. Water is added in a quantity sufficient (q.s.) to provide the desired composition and the composition is mixed until homogenous.

Methods of using the present composition are provided and are included within the scope of the present invention. In general, such methods comprise administering a composition in accordance with the present invention to a peripheral location of a human or animal, thereby obtaining a desired therapeutic effect. A syringe apparatus including an appropriately sized needle, for example, a 27 gauge needle or a 30 gauge needle, can be effectively used to inject the composition.

The present methods may comprise a single injection into a peripheral location or may involve repeated injections, for example over periods of time ranging from about one week or about 1 month or about 3 months to about 6 months or about 1 year or longer.

EXAMPLES

The following non-limiting Examples are presented to exemplify aspects of the present invention.

Examples 1 to 4

Four compositions are as follows:

TABLE 1

| Ingredient | Example 1 | Example 2 | Example 3 | Example 4 |
|---|---|---|---|---|
| Triamcinolone acetonide | 2% (w/v) | 2% (w/v) | 4% (w/v) | 4% (w/v) |
| Sodium Hyaluronate ($0.6 \times 10^6$ DALTONS) | 0.05% (w/v) | 0.5% (w/v) | 0.05% (w/v) | 0.5% (w/v) |
| Sodium Phosphate | 0.4% (w/v) | 0.4% (w/v) | 0.4% (w/v) | 0.4% (w/v) |
| Vitamin E-TPGS | 0.5% (w/v) | 0.5% (w/v) | 0.0 | 0.0 |
| γ-cyclodextrin | 0.5% (w/v) | 0.5% (w/v) | 0.0 | 0.0 |
| Water for Injection | q.s. | q.s. | q.s. | q.s. |
| Viscosity at shear rate 0.1/second at 25° C. | 20 cps | 500 cps | 20 cps | 500 cps |

Each of these compositions is prepared as follows.

A concentrated triamcinolone acetonide dispersion is made by combining triamcinolone acetonide with water, Vitamin E-TPGS and γ-cyclodextrin, if any. These ingredients are mixed to disperse the triamcinolone acetonide, and then autoclaved. The sodium hyaluronate may be purchased as a sterile powder or sterilized by filtering a dilute solution followed by lyophylization to yield a sterile powder. The sterile sodium hyaluronate is dissolved in water to make an aqueous concentrate. The concentrated triamcinolone acetonide dispersion is mixed and added as a slurry to the sodium hyaluronate concentrate. Water is added q.s. (quantum sufficit, as much as suffices, in this case as much as is required to prepare the homogenous mixture, dispersion, gel or suspension) and the mixture is mixed until homogenous.

Each of these compositions produced a loose flocculation of triamcinolone acetonide that is easily re-suspended by gentle inversion. These compositions can be marketed in small volume pharmaceutical grade glass bottles, and are found to be therapeutically effective against various peripheral conditions when peripherally administered.

Examples 5 to 7

Three compositions are as follows:

TABLE 2

| Ingredient | Example 5 | Example 6 | Example 7 |
|---|---|---|---|
| Triamcinolone acetonide | 2.0% (w/v) | 4.0% (w/v) | 8.0% (w/v) |
| Sodium hyaluronate | 3.0% (w/v) | 2.5% (w/v) | 2.0% (w/v) |
| Sodium Phosphate | 0.4% (w/v) | 0.4% (w/v) | 0.4% (w/v) |
| Water for Injection | q.s. | q.s. | q.s. |
| Viscosity at shear rate 0.1/second at 25° C. | 300,000 cps | 180,000 cps | 100,000 cps |

These compositions are prepared in a manner substantially analogous to that set forth in Example 1.

The high viscosities of the compositions substantially slows the particle sedimentation rate to an extent that no resuspension processing is necessary or required over the estimated shelf life, e.g., about 2 years, of the compositions. These compositions can be marketed in prefilled syringes since they can not easily be removed by a needle and syringe from a container. However, with the compositions in prefilled syringes, the compositions can be effectively injected intramuscular or intra-articular using a 27 gauge or a 30 gauge needle to provide a desired therapeutic effect.

The compositions of Examples 5 to 7 employ or contain a sufficient concentration of high molecular weight sodium hyaluronate so as to form a gelatinous plug or drug depot upon peripheral administration to a peripheral location. Triamcinolone acetonide particles are, in effect, trapped or held within this viscous plug, so that undesirable pluming does not occur, and the risk of drug particles disadvantageously settling directly on the tissue is substantially reduced, for example, relative to using a composition with a water-like viscosity, such as Kenalog® 40. Since sodium hyaluronate solutions are subject to dramatic shear thinning, these formulations are easily injected through 27 gauge or even 30 gauge needles.

Examples 8 and 9

Two compositions are as follows:

TABLE 3

| Ingredient | Example 8 | Example 9 |
|---|---|---|
| Triamcinolone acetonide | 2.0% (w/v) | 8.0% (w/v) |
| Sodium hyaluronate (polymeric) | 2.5% (w/v) | 2.3% (w/v) |
| Sodium chloride | 0.63% (w/v) | 0.63% (w/v) |
| dibasic sodium phosphate, heptahydrate | 0.30% (w/v) | 0.30% (w/v) |
| Monobasic sodium phosphate, monohydrate | 0.04% (w/v) | 0.04% (w/v) |
| Water for Injection | q.s. | q.s. |
| Viscosity at shear rate 0.1/second at 25° C. | 170,000 ± 25% cps | 200,000 ± 25% cps |

These compositions are prepared in a manner substantially analogous to that set forth in Example 1.

The high viscosities of the compositions substantially slows the particle sedimentation rate to an extent that no resuspension processing is necessary or required over the estimated shelf life, e.g., about 2 years, of the compositions. These compositions can be marketed in prefilled syringes since they can not easily be removed by a needle and syringed from a container. However, with the compositions in prefilled syringes, the compositions can be effectively injected into a peripheral location using a 27 gauge or a 30 gauge needle to provide a desired therapeutic effect.

The sodium hyaluronate powders used in these compositions (as well as in the other compositions identified in the Examples herein) have water contents in a range of about 4% to about 20%, preferably about 4% to about 8%, by weight. Differences in the average molecular weight of the hyaluronate used can result in variation in the viscosity of compositions in accordance with the present invention which have the same nominal chemical make-ups. Thus, the viscosities indicated herein should be understood to be target viscosities, with the composition being acceptable for use if the actual viscosity of the composition is within plus or minus (±) about 25% or about 30% or about 35% of the target viscosity.

Because each of the compositions set forth in the Examples has a density of about 1 gm/ml, the percentages set forth herein as being based on weight per volume (w/v) can also be considered as being based on weight per weight (w/w).

The compositions of Examples 8 and 9 employ or contain a sufficient concentration of high molecular weight (i.e. polymeric) sodium hyaluronate so as to form a gelatinous plug or drug depot upon peripheral injection into s peripheral location. Preferably the average molecular weight of the hyaluronate used is less than about 2 million, and more preferably the average molecular weight of the hyaluronate used is between about 1.3 million and 1.6 million. The triamcinolone acetonide particles are, in effect, trapped or held within this viscous plug of hyaluronate, so that undesirable pluming does not occur upon peripheral injection of the formulation. Thus, the risk of drug particles disadvantageously settling directly on tissues is substantially reduced, for example, relative to using a composition with a water-like viscosity, such as Kenalog® 40. Since sodium hyaluronate solutions are subject to dramatic shear thinning, these formulations are easily injected through 27 gauge or even 30 gauge needles.

The most preferred viscosity range for the Example 8 and 9 formulations is 140,000 cps to 280,000 cps at a shear rate 0.1/second at 25° C.

The triamcinolone acetonide used in the formulations set forth herein has the is chemical name 9-Fluoro-11,21-dihydroxy-16,17-[1-methylethylidenebis(oxy)]pregna-1,4-diene-3,20-dione, and can have the following structure

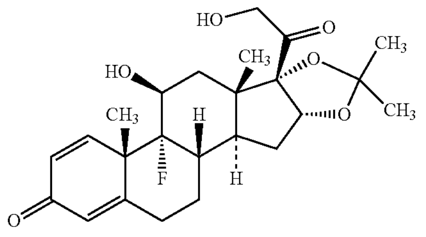

The molecular formula of triamcinolone acetonide is $C_{24}H_{31}FO_6$ and its molecular weight is 434.49. Triamcinolone acetonide has a very low solubility in water of only about 0.11 mg/ml to about 0.13 mg/mL. Loftsson T. et al., *Determination of Aqueous Solubility by Heating and Equilibration: A Technical Note, AAPS PharmSciTech.* 2006; 7(1): Article 4.DOI: 10.1208/pt070104, and; Yang J. et al., *Transdermal delivery system of triamcinolone acetonide from a gel using phonophoresis*, Arch Pharm Res 29(5); 412-417: 2006.

The Examples 8 and 9 formulations are prepared as sterile products of a uniform, opaque white dispersion of microfine triamcinolone acetonide particles suspended in a hyaluronate-based polymeric hydrogel, intended for peripheral injection.

The Examples 8 and 9 formulations can be used to treat, for example, arthritis (i.e. rheumatoid and osteoarthritis) and various allergic and dermatologic conditions. Notably the Examples 8 and 9 formulations are formulated using only excipients that are fully biocompatible (i.e. non-toxic). The Examples 8 and 9 formulations (2% (w/w) and 8% (w/w) triamcinolone acetonide, respectively) are buffered at physiological pH with a low concentration of sodium phosphate salts; rendered isotonic with sodium chloride, and use Water for Injection, USP, as the vehicle.

A target dosage of 1 mg of the triamcinolone acetonide active agent can be delivered in a 50 mg (approximately 48 μL) injection of the Example 8 2% (w/w) triamcinolone acetonide gel suspension formulation. A target dosage of 4 mg of the triamcinolone acetonide active agent can be delivered in a 50 mg (approximately 48 μL) injection of the Example 9 8% (w/w) triamcinolone acetonide gel suspension formulations.

As noted, the triamcinolone present in our formulations does not rapidly, or even slowly, settle out from or precipitate from the formulations. Significantly our Example 8 and 9 formulations have a shelf life of at least two years, meaning that these formulations can be left standing (without agitation) for up to about two years before peripheral administration, and after two years the same formulations can still provide a consistent and accurate dose of triamcinolone upon injection to the formulation. For example, upon preparation (as set forth in Example 15), 50 μL of our 8% formulation provides 4 mg of triamcinolone acetonide, and if left standing for up to about 2 years 50 μL of our 8% formulation stills provides 4 mg±15% of triamcinolone acetonide, thereby meeting the U.S.P. definition of consistent dosage after storage.

As noted, the composition of triamcinolone 2% injectable gel suspension (Example 8) is triamcinolone 2.0% (w/w), sodium hyaluronate, sodium chloride, dibasic sodium phosphate (heptahydrate), monobasic sodium phosphate (monohydrate), and water for injection). The composition of triamcinolone 8% injectable gel suspension (Example 9) is triamcinolone 8.0% (w/w), sodium hyaluronate, sodium chloride, dibasic sodium phosphate (heptahydrate), monobasic sodium phosphate (monohydrate), and water for injection.

The triamcinolone acetonide injectable gel suspension we have invented is a viscous suspension of triamcinolone acetonide formulated at concentrations of 8% and 2% with sodium hyaluronate, sodium chloride, dibasic sodium phosphate (heptahydrate), monobasic sodium phosphate (monohydrate), and water for injection (i.e. the formulations of Examples 8 and 9 respectively). The suspensions are prepared to have physiologic pH, and to be isotonic, and preservative-free. The Examples 8 and 9 suspensions can be supplied in single-use glass syringes with fixed 27 gauge needles. The syringes are overfilled to 0.17-0.18 mL, and calibrated to deliver 0.05 mL when primed to a black or blue mark on the barrel of the syringe to thereby provide the 2% and 8% suspensions to deliver 1 mg and 4 mg of triamcinolone, respectively (the pre-filled syringes are made by Allergan, Inc., Irvine, Calif.). These syringes have a shelf life of at least about two years when stored at 2-8° C.

Example 10

Triamcinolone Gel Suspensions to Treat Peripheral Conditions

A preferred formulation, such as that of Examples 8 and 9 can be used to treat a peripheral condition by intramuscular injection, but formulated to contain up to 160 mg of the triamcinolone in the formulation injected. The injection is carried out by intramuscular injection into the gluteal muscles of either or both legs to treat eg an acute exacerbation of multiple sclerosis symptoms. Hay fever can be treated by injecting the gluteal muscle with the Example 8 or Example 9 formulation formulated to contain 40 to 80 mg (i.e. 60 mg) of the triamcinolone.

Articular disorders can be treated by intra-articular injection of the Example 8 or Example 9 formulation formulated to contain 2.5 to 5 mg triamcinolone (for a smaller joint and from 5 to 40 mg triamcinolone for a larger joint.

Intramuscular or intra-articular administration of the Example 8 or Example 9 formulation can be use to treat pain (as in arthritis, such as osteoarthritis) administering (a) a cross-linked (with more cross-linking the hyaluronic acid will reside in the joint for a longer period) or not cross-linked hyaluronic acid, followed by (b) administration of a steroid (i.e. 1-8 wt % triamcinolone (for a greater effect to decrease inflammation) followed by (c) administration of just a hyaluronic acid by itself.

An alternate method can be intramuscular or intra-articular administration of the Example 8 or Example 9 formulation followed by use of a hyaluronic acid by itself (for the lubrication and anti-inflammation effect of the hyaluronic acid).

These methods have the advantage of no post-injection flare and permit use of a small gauge needle due to the high shear thinning when use the disclosed hyaluronic acid, even though the hyaluronic acid has a high viscosity at rest.

Our invention comprises triamcinolone acetonide injectable gel suspensions formulated viscous suspensions of triamcinolone acetonide at concentrations of, for example, 8% and 2% with sodium hyaluronate, sodium chloride, dibasic sodium phosphate (heptahydrate), monobasic sodium phosphate (monohydrate), and water for injection. The triamcinolone acetonide injectable gel suspensions are preferably at physiologic pH, isotonic, and preservative-free. Triamcinolone acetonide injectable gel suspensions within the scope of our invention can be supplied in single-use glass syringes with fixed 27 gauge needles. The syringes can be overfilled to 0.17-0.18 mL, and calibrated to deliver 0.05 mL when primed to a black mark on the barrel of the syringe to thereby deliver, for example, 2% and 8% suspensions of 1 mg and 4 mg of triamcinolone, respectively. Our triamcinolone acetonide injectable gel suspensions can be defined as implants which upon injection (i.e. implantation) into a peripheral location provided sustained release (i.e. over a period of up to seven months or longer) from the compact gel bolus injected.

Significantly, in our formulations the triamcinolone particles (crystals) are not available to and/or are substantially ignored by macrophages due to the aggregation (suspension) of the triamcinolone particles in the high molecular weight hyaluronate used in our formulations. The fact that our triamcinolone formulations are in situ forming implants can also limit the exposure of whole or individual triamcinolone crystals to sensitive peripheral tissues, concomitantly thereby limiting macrophage activation and hence also limiting or preventing an peripheral inflammatory response. It is important to note that with our formulation the particular high viscosity hyaluronic acid polymer chosen maintains the triamcinolone crystals in a collective matrix that acts as a sustained-release reservoir which decrease the need for frequent repeat injections. Thus, our formulation forms a cohesive agglomerate upon peripheral injection. The reduced surface area of such an agglomerate facilitates provision and maintenance of a lower release rate of the triamcinolone, as compared to much larger surface area saline suspension of a triamcinolone (such as Kenalog). The cohesiveness of our formulation is exemplified by the fact that the formulation maintains its internal consistency (i.e. its shape after injection) for at least about 30 weeks after injection.

Additionally, the compositions of our invention are preferably formulated with hyaluronic acid, a material known for its anti-inflammatory abilities. Dea I. et al., *Hyaluronic acid: a novel, double helical molecule*, Science, 1973 Feb. 9; 179 (73):560-2.).

Furthermore, the absence of preservatives and/or stabilizers (such as benzyl alcohol and polysorbate 80) in our formulation reduces the retinal toxicity of our formulations as compared to formulations which contain one or more preservatives and/or stabilizers.

The combination of these five factors (lack of injury to macrophages, low availability of the triamcinolone crystal to macrophages, use of a biocompatible polymer, use of a high viscosity biocompatible polymer, and absence of preservatives and stabilizers provides an optimal delivery system which limits the incidence of post-injection aseptic endophthalmitis.

A preferred embodiment of our invention can be the Example 8 and 9 formulations in which the average diameter of the triamcinolone particles present in the formulations is less than 10 microns and preferably less than 5 microns, and additionally with a uniform (spherical) morphology. It has been shown in the pulmonary literature that micronized particles of corticosteroids, <10 microns, and preferably <5 microns, are less injurious to macrophages, and have the potential for less inflammation. Thus, preparing our formulations with a median triamcinolone particle size of <5 microns and with uniform shape provides formulation which are even more biocompatible in the peripheral and with less propensity to cause peripheral location inflammation.

Example 11

Method for Making Injectable Triamcinolone Acetonide Gel Suspension Formulations Preferred methods were developed for making the formulations of Examples 1 to 9.

The triamcinolone formulations are made as sterile, uniform, opaque white gel suspensions suitable for peripheral injection. The manufacturing process involves two main stages: 1) sterile suspension bulk compounding and 2) aseptic filling. The bulk product manufacture includes preparations of three separate parts, followed by aseptic combination of these three parts. The aseptic filling operation is conducted in a class 100 environment, and the sterile bulk product may be filled into pre-sterilized ready-to-use syringes.

Micronized triamcinolone acetonide, USP, was purchased from Pfizer, Inc., Kalamazoo Mich. Typical and most useful particle sizes for this drug are 4-8 microns in diameter. Sodium hyaluronate powder was purchased from Hyaluron, Woburn, Mass. Typical and most useful molecular weights for this polymer are 1.0 to 1.9 million Daltons. When used, SBE7-3-cyclodextrin (Captisol®) was obtained from CyDex, Inc., Overland Park, Kans.

Part I is prepared in a main batch vessel that has capabilities of bulk heat sterilization and viscous fluid mixing. First, water for injection (WFI) at 40% of batch size is charged into the vessel and sodium chloride is dissolved. Triamcinolone powder is then added and dispersed with strong agitation. The suspension is heated and sterilized at above 121° C. for a sufficient time period by steam passing through the jacket of the vessel. After the bulk heat cycle is completed, the suspension is cooled down to room temperature.

Part II is prepared in an open vessel equipped with a top entering, variable speed mixer. First, WFI at 10% of batch size is charged into the vessel. Sodium phosphate salts and, optionally, a β-cyclodextrin derivative is added and dissolved. If necessary, the pH of the solution is adjusted with 1 N sodium hydroxide and/or 1 N hydrochloric acid. When a beta cyclodextrin is used in the formulation is can be dissolved along with the phosphate salts in this part II.

Part III is prepared in a Class 100 environment through a series of aseptic procedures. First, sodium hyaluronate is dissolved in WFI at dilute concentration, e.g., 0.2% w/w. The solution is sterile-filtered and sodium hyaluronate powder is recovered through bulk lyophilization. Finally, the sodium hyaluronate powder is reconstituted with sterile WFI at 50% of batch size.

Sterile bulk suspension is compounded by aseptically combining (mixing) the three parts. First, Part II solution is filtered into sterile Part I in the main batch vessel using a 0.2 micron sterilizing grade filter. Part III is then aseptically transferred into the main batch vessel. Finally, the bulk is blended (mixed) under low shear conditions to achieve uniformity. The final bulk suspension is held in a controlled area before aseptic filling.

Aseptic filling operations are performed in a Class 100 environment. Sterile bulk suspension is first filtered through a clarification screen into a sterile holding container. The bulk is then transferred to the filling machine and filled into pre-sterilized syringes. The filled units are transferred to the packaging area for application of tamper-evident seals, labeling and cartoning.

The pharmaceutical manufacturing process of this Example 15 for making triamcinolone sterile suspensions is illustrated by the FIG. 1 process flow chart.

Although not shown in FIG. 1, after Part III has been made (and before the lyophilization step is applied to Part III), Part III can be heated at between about 120° C. and about 130° C. for between about 25-35 minutes. Doing so both sterilizes the hyaluronate and can reduce the initial 1 million to 1.9 million Daltons molecular weight of the hyaluronate used in our formulation by about 20% to about 30% (i.e. to between about 0.7 million to about 1.3 million Daltons), thereby permitting use of a higher (i.e. 30 gauge) gauge injection needle.

Example 12

Low Immunogenicity, Stable Peripheral Triamcinolone Compositions

The formulation of Example 9, a viscous formulation comprising 2-8 wt % triamcinolone acetonide in polymeric hyaluronic acid, referred to herein by the trade name Trivaris. The findings set forth herein apply as well to the Example 8 formulation (Trivaris 2%). We confirmed the low immunogenicity or anti-inflammatory nature of Trivaris and determined that upon administration substantially all the Trivaris triamcinolone acetonide particles are embedded within the polymeric matrix of the hyaluronic acid and that Trivaris is storage stable.

A major factor associated with the inflammatory reaction characteristic of sterile endophthalmitis can be the drug particle burden at the site of peripheral administration, as evidenced by the plume effect, which can occur upon peripheral injection of an aqueous (low viscosity) TA formulation. Thus, individual drug particles are recognized by resident macrophages as they attempt to phagocytose free floating drug particles. Phagocytosis leads to cytokine release and both neutrophils and macrophages are thereby recruited. The enormous numbers of indigestible drug particles released by an aqueous TA formulation (with or without a preservative) can be lethal to macrophages and neutrophils, causing these cells die and release lysosomal contents, oxidative enzymes, and more proinflammatory cytokines. This results in an acceleration of the inflammatory reaction and hence the clinical manifestations of sterile endophthalmitis.

Due to their higher density triamcinolone acetonide drug particles injected the agglomerate into consolidated drug depots within the first week following peripheral injection. Therefore, the risk of sterile endophthalmitis occurring is generally within the 48 hour period after injection as this is the time when the macrophages have greatest access to the still free floating, individual drug particles.

Three lots of Kenalog-40 were examined (see FIG. 2) and it was determined that the TA particles in Kenalog can be as large as 80 microns, with high particles size variability. The heterogeneous population of drug particles in Kenalog-40 ranging in size from about 2 to about 80 microns can be injurious to phagocytes since larger and irregularly shaped drug particles are poorly ingested by such cells resulting in phagocyte cell death. This toxic inflammatory reaction to corticosteroid crystals has also been observed following intra-articular injections where an inflammatory joint reaction occurs within 48 hours after injection is called crystal synovitis. Other more remote causes of sterile endophthalmitis with use of peripheral corticosteroid formulations include the presence of endotoxins, extraneous particles and/or excipients in the formulation and the formulation having a pH less than 5 or greater than pH 8.

The particles size distribution of four lots of triamcinolone acetonide particles (raw material) used to make the various Trivaris formulations was also examined. As shown by FIGS. 3A to 3D, the median TA particles size was between about 4 microns and 5 microns and 90% of the TA particles had a diameter of 10 microns or less. FIG. 3 also shows that about 40% of the TA particles had a diameter between about 4 microns and about 8 microns and that about 60% of the TA particles had a diameter between about 3.5 microns and about 9 microns. The TA particle size distribution data in FIGS. 2 and 3 was obtained by light scattering using a Horiba LA 300 instrument. The line graph in FIGS. 3A, B, C and 3D shows the cummulative TA particle size % (area under the curve) (right hand side Y axis).

Trivaris is a viscous TA formulation in which the TA drug particles are embedded in and coated by the polymeric matrix of the hyaluronic acid (HA) to thereby form a viscoelastic hydrogel with a viscosity of between about 130 k and about 300 k centipoises (cps) at a shear rate of about 0.1/second at 25° C. Significantly, the TA drug particle sizes in Trivaris are deliberately uniform in distribution with a median particle size ranging from about 4 to about 6 microns. This hydrogel formulation of Trivaris can be injected through a hypodermic (syringe) needle having a needle gauge as small as 33 gauge.

The HA in Trivaris creates a physical barrier to free movement of the embedded TA drug particles, thereby reducing the potential for free floating TA particle exposure in the peripheral and resulting macrophage activation. Importantly, HA is recognized by scavenging peripheral macrophages as a native (non-immunogenic) because there is a high concentration of HA naturally present in the peripheral humor. Thus coating the TA drug particles with HA renders the injected Trivaris formulation non-antigenic, lowering the potential of the TA drug particles to instigate an inflammatory response. Use of HA encapsulation as an 'immunologic disguise' is used in a similar fashion by some streptococcus bacterial species to evade detection and phagocytosis by macrophages and increasing the virulence of the organism. Importantly, the hydrogel formulation of Trivaris permits the TA particles to become free drug as the TA is solubilized (dissolves), thereby permitting the solubilized TA to enter solution and then diffuse or be actively transported to the retina to treat a retinal disease or condition. The close proximity of the TA drug particles in the Trivaris HA hydrogel allows for controlled and rapid agglomeration of the TA particles as the HA gradually diffuses over time out of the depot formed upon peripheral Trivaris injection.

The low numbers of drug particles in an unbound state following injection of Trivaris can be expected to reduce activation of scavenging macrophages compared with other TA suspensions, such as Kenalog-40, where the majority of the TA particles are upon peripheral injection exposed to macrophages and inflammatory consequences can then ensue. The effectiveness of the Trivaris formulation to reduce the inflammatory potential.

A further experiment was carried out to examine the stability of the TA particles in Trivaris. We determined that the TA drug particles in the HA hydrogel suspension of Trivaris were remarkably stable, with minimal crystal agglomeration or degradation during extended storage. Thus, 0.5 mL glass syringes were filled with 0.2 mL of the Example 9 formulation. The filled syringes were stored horizontally at 25° C. in 60% relative humidity. Upon syringe filling (time zero), at 5 weeks, at 6 weeks and after three months of storage, TA particle size was determined using laser light scattering with Horiba LA 300 instrument, after dilution of a Trivaris sample in distilled water just prior to the light scattering analysis. 90th percentile of volume-weighted size distribution data from three different lots showed that at time zero 90% of the TA particles had a diameter of 11 microns or less, at +5 weeks and at +6 weeks 90% of the TA particles still had a diameter of about 11 microns or less. Finally at +3 months 90% of the TA particles still had a diameter of about 13 microns or less. These results mean that even with prolonged storage the TA particles remain suspended in the HA and undergo neither substantial agglomeration or degradation. Hence, even after prolonged storage Trivaris retains its syringeability without needle occlusion.

In addition to limiting particle exposure, the HA of Trivaris has additional inherent anti-inflammatory properties. Hyaluronic acid inhibits movement of macrophages, down regulates the production of proinflammatory cytokines and chemokines in models and human diseases, scavenges oxygen free radicals, and inhibits matrix metalloproteinases. Trivaris can include additional features to minimize an inflammatory reaction upon peripheral injection, such as preparing Trivaris to have a pH between 6 and 7 range, and strict endotoxin and extraneous particle control.

Furthermore, the uniform population of micronized TA particles used to make Trivaris (see FIG. 3) provides a predictable peripheral TA release pharmacokinetics with increased TA peripheral half-life.

The Example 8 and 9 Trivaris formulations can also be used as an injectable pharmaceutical composition to treat various articular (joints and spine) pathologies while at the same time reducing the potential for occurrence of post-injection inflammation (crystal synovitis).

In summary, the Trivaris formulation creates a physical barrier to free movement of drug particles to reduce the potential for particle exposure, macrophage activation, and the potential for sterile endophthalmitis. The consolidation of the TA drug particles in the HA hydrogel enables immediate recovery of vision after injection & enables PDT, thermal laser and diagnostic procedures to be performed. Incorporating a uniform population of micronized TA particles in the formulation facilitates management by macrophages when outside of the drug depot, but also leads to predictable peripheral pharmacokinetics with an increased peripheral half-life. Trivaris is supplied in pre-loaded syringes with little or no endotoxin and extraneous particle content, to thereby further limit post-injection inflammation. Trivaris is formulated to not contain benzyl alcohol or any other preservatives thereby reducing toxicity to peripheral location tissues upon peripheral administration of the formulation.

Example 13

Drug or Biologic-Hyaluronic Acid Formulations

A 50:50 blend of 8% Trivaris with Juvederm (final concentration 4% triamcinolone acetonide) was formulated. The physical blending of the two components was not difficult to accomplish and the formulation was syringeable through a 25 g needle.

An experiment can be carried out to evaluate the rate of release of a drug (i.e. cyclosporine, rapamycin or steroid such as triamcinolone acetonide) or a biologic (such as a botulinum toxin) from a high viscosity, high molecular weight carrier such as a polymeric hyaluronic acid. It can be determined that the rate of drug release of the drug or biologic is a function of extent of cross-linking of monomers of the polymeric carrier. For example, a botulinum toxin (such as BOTOX, DYSPORT, XEOMIN or MYOBLOC) can be formulated with a cross-linked hyaluronic acid to and administered as a dermal filler and wrinkle remover, thereby providing a prolonged residency of the botulinum toxin at the site of dermal administration and concomitantly a prolonged anti-wrinkle effect by the botulinum toxin. U.S. patent application publication number 2005 244358 discloses a method for reducing dermal lines by subdermal administration of a viscous chondroitin sulfate, hyaluronic acid and botulinum toxin type A composition.

While this invention has been described with respect to various specific examples and embodiments, it is to be understood that the invention is not limited thereto. For example, the corticosteroid formulations set forth herein can be used to treat conditions including articular pathologies, such as rheumatoid and osteoarthritis, and spinal conditions, such as facet arthritis, and the treatment of chronic pain by epidural or spinal root injections of a formulation such as a Trivaris formulation Additionally, although preferably the polymeric hyaluronate in Trivaris is a non-cross linked hyaluronate (so as to obtain, upon application of force to the plunger of the syringe used to administer Trivaris, a high shear rate and hence relative ease of injection of Trivaris through a 27-33 gauge needle), the hyaluronate can alternately be a cross linked hyaluronate (to form a true hydrogel therefore) with a significantly lower viscosity (i.e. with a viscosity of about 5,000 cps at a shear rate of about 0.1/second at about 25° C.). Such a cross-linked hyaluronate can have the same or similar excellent corticosteroid suspension property of Trivaris, and have the additional advantage of longer residency (i.e. biodegradable at a slower rate) of the hyaluronate in the peripheral, with resulting prolonged nominal immunogenicity of such a cross-linked hyaluronate formulation in the peripheral, due to a longer period of peripheral (or peripheral) retention of the corticosteroid particles in the polymeric matrix of the cross-linked hyaluronate. Cross-linked and non-cross linked hyaluronans can also be blended in various proportions to optimize syringeability while slowing biodegradation and improving long-term retention within inflammed tissues, such as in the treatment of osteoarthritis.

Furthermore, besides cross-linked hyaluronate other cross-linked polymers can be used, such as for example a polycarbophil.

All references, articles, publications, patents and applications set forth above are incorporated herein by reference in their entireties.

We claim:

1. A method for treating a spine condition, the method comprising the step of injecting into the vertebral column of a patient with a spine condition a viscous formulation comprising a plurality of triamcinolone particles, the plurality of triamcinolone particles having a media particle size of less than about 10 microns, mixed into a viscous polymeric matrix, wherein the viscous formulation has a viscosity of between about 130,000 cps and about 300,000 cps at a shear rate of about 0.1/second at about 25° C., and wherein the polymeric matrix comprises a) a cyclodextrin component and b) polymeric hyaluronate or a polymeric hyaluronic acid, and wherein the spine condition is selected from the group consisting of radiculopathy, spondylitis, and spondylosis.

2. The method of claim 1, wherein the triamcinolone is triamcinolone acetonide.

3. The method of claim 1, wherein the triamcinolone is triamcinolone hexacetonide.

4. The method of claim 1, wherein the cyclodextrin component is selected from the group consisting of β-cyclodextrin and sulfobutylether β-cyclodextrin.

5. The method of claim 1, wherein the triamcinolone is present in an amount of about 30% (w/v).

6. The method of claim 1, wherein the triamcinolone is present in an amount in the range of 10% (w/v) to 20% (w/v).

7. The method of claim 1, wherein the triamcinolone is present in an amount of 5% (w/v) to 10% (w/v).

8. The method of claim 1, wherein the injection into the vertebral column is with dose of triamcinolone in the range of 5 mg to 40 mg.

* * * * *